US011531024B2

(12) United States Patent
Baird et al.

(10) Patent No.: US 11,531,024 B2
(45) Date of Patent: Dec. 20, 2022

(54) MASS TAG ANALYSIS FOR RARE CELLS AND CELL FREE MOLECULES

(71) Applicant: Purdue Research Foundation, West Lafayette, IN (US)

(72) Inventors: Zane Baird, West Lafayette, IN (US); Robert Graham Cooks, West Lafayette, IN (US); Adam Hollerbach, West Lafayette, IN (US); Zheng Ouyang, West Lafayette, IN (US); Michael Pugia, Elkhart, IN (US)

(73) Assignee: Purdue Research Foundation, West Lafayette, IN (US)

( * ) Notice: Subject to any disclaimer, the term of this patent is extended or adjusted under 35 U.S.C. 154(b) by 528 days.

(21) Appl. No.: 15/762,597

(22) PCT Filed: Sep. 24, 2016

(86) PCT No.: PCT/US2016/053610
§ 371 (c)(1),
(2) Date: Mar. 23, 2018

(87) PCT Pub. No.: WO2017/053911
PCT Pub. Date: Mar. 30, 2017

(65) Prior Publication Data

US 2018/0275118 A1 Sep. 27, 2018

Related U.S. Application Data

(60) Provisional application No. 62/222,940, filed on Sep. 24, 2015.

(51) Int. Cl.
*G01N 33/53* (2006.01)

(52) U.S. Cl.
CPC ..... *G01N 33/5302* (2013.01); *G01N 2458/15* (2013.01)

(58) Field of Classification Search
CPC ......... G01N 33/5302; G01N 33/48721; G01N 2458/15; G01N 15/1031
See application file for complete search history.

(56) References Cited

U.S. PATENT DOCUMENTS 5,182,213 A 1/1993 Genshaw et al.
7,335,897 B2 2/2008 Takats et al.
(Continued)

FOREIGN PATENT DOCUMENTS

WO 2013/184320 A1 12/2013

OTHER PUBLICATIONS

Harrell, C. Chad, et al. "Resistive-pulse DNA detection with a conical nanopore sensor." Langmuir 22.25 (2006): 10837-10843. (Year: 2006).*

(Continued)

*Primary Examiner* — Robert J Eom
(74) *Attorney, Agent, or Firm* — Brown Rudnick LLP; Adam M. Schoen

(57) ABSTRACT

The invention generally relates to mass tag analysis for rare cells and cell free molecules. In certain embodiments, the invention provides an apparatus including an essentially non-absorbent membrane having at least one pore, a microwell operably associated with the essentially non-absorbent membrane, and an electric field generator. The apparatus may be configured such that an electric field produced by the electric field generator operably interacts with a sample in the microwell and expels a droplet of the sample through the at least one pore in the essentially non-absorbent membrane. In certain embodiments, apparatuses of the invention are used for detection, and optionally quantification, of a target analyte from a heterogeneous sample, such as a rare target analyte (e.g., rare cell) from a biological sample.

9 Claims, 11 Drawing Sheets

(56) References Cited

U.S. PATENT DOCUMENTS

| | | | |
|---|---|---|---|
| 8,519,354 B2 | 8/2013 | Charipar et al. | |
| 8,859,956 B2 | 10/2014 | Ouyang et al. | |
| 9,184,036 B2 | 11/2015 | Cooks et al. | |
| 2005/0001161 A1 | 6/2005 | Hafeman et al. | |
| 2005/0116161 A1 | 6/2005 | Hafeman et al. | |
| 2005/0230635 A1 | 10/2005 | Takats et al. | |
| 2008/0001525 A1 | 6/2008 | Chang et al. | |
| 2008/0152509 A1 | 6/2008 | Chang et al. | |
| 2009/0000718 A1 | 3/2009 | Hafeman et al. | |
| 2009/0071834 A1 | 3/2009 | Hafeman et al. | |
| 2010/0122907 A1* | 5/2010 | Stanford .......... | G01N 33/48721 204/451 |
| 2011/0042560 A1 | 2/2011 | Ouyang et al. | |
| 2012/0119079 A1 | 5/2012 | Ouyang et al. | |
| 2013/0000388 A1 | 2/2013 | Schultz et al. | |
| 2013/0038868 A1 | 2/2013 | Schultz et al. | |
| 2013/0002808 A1 | 10/2013 | Cooks et al. | |
| 2013/0280819 A1 | 10/2013 | Cooks et al. | |
| 2014/0001588 A1 | 1/2014 | Veis | |
| 2014/0158881 A1 | 6/2014 | Cooper | |
| 2014/0002487 A1 | 9/2014 | Monbouquette et al. | |
| 2014/0248711 A1 | 9/2014 | Monbouquette et al. | |

OTHER PUBLICATIONS

Baaken, Gerhard, et al. "Nanopore-based single-molecule mass spectrometry on a lipid membrane microarray." Acs Nano 5.10 (2011): 8080-8088. (Year: 2011).*

Tang, Keqi, et al. "Generation of multiple electrosprays using microfabricated emitter arrays for improved mass spectrometric sensitivity." Analytical Chemistry 73.8 (2001): 1658-1663. (Year: 2001).*

Wang, Ying-Xin, et al. "Efficient electrospray ionization from polymer microchannels using integrated hydrophobic membranes." Lab on a Chip 4.4 (2004): 363-367. (Year: 2004).*

Ammann, Adrian A. "Inductively coupled plasma mass spectrometry (ICP MS): a versatile tool." Journal of mass spectrometry 42.4 (2007): 419-427. (Year: 2007).*

Balakin, Alexander A., Vladimir V. Gridin, and Israel Schechter. "Track membrane mediated electrostatic introduction of cluster ions into TOF mass spectrometer." The Journal of Physical Chemistry A 102.47 (1998): 9470-9475. (Year: 1998).*

Extended European Search Report for EP Application No. 16849824.4 dated Jan. 9, 2019, 8 pages.

Fico, 2007, Miniaturization and Geometry Optimization of a Polymer-Based Rectilinear Ion Trap, Anal. Chem., vol. 79: pp. 8076-8082.

Gao, 2006, Handheld Rectilinear Ion Trap Mass Spectrometer, Anal. Chem., 78:5994-6002.

Gao, 2008, Design and Characterization of a Multisource Hand-Held Tandem Mass Spectrometer, Z. Anal. Chem, 80:7198-7205.

Hou, 2011, Sampling Wand for an Ion Trap Mass Spectrometer, Anal. Chem., 83:1857-1861.

Kogelschatz, 2003, Dielectric-barrier Discharges: Their History, Discharge Physics, and Industrial Applications, Plasma Chemistry and Plasma Processing, 23:1-46.

Köhler, 1975, Continuous cultures of fused cells secreting antibody of predefined specificity, Nature vol. 265:495-497.

Melchers, Lymphocyte Hybridomas, 1978, Springer-Verlag (New York 1978).

Galfre, 1981, Preparation of Monoclonal Antibodies: Strategies and Procedures, Methods of Enzymology 73 (Part B): 3-46.

Mulligan, 2006, Desorption electrospray ionization with a portable mass spectrometer: in situ analysis of ambient surfaces, Chem. Comm., 1709-1711.

Mulligan, 2006, Direct monitoring of toxic compounds in air using a portable mass spectrometer, The Analyst 131:556-567.

Ouyang, 2009, Handheld Miniature Ion Trap Mass Spectrometers, Anal. Chem., vol. 81: pp. 2421-2425.

Ouyang, 2009, Miniature Mass Spectrometers, Ann. Rev. Anal. Chem., 2:187-214.

Sanders, 2009, Hand-held Mass Spectrometer for Environmentally Relevant Analytes Using a Variety of Sampling and Ionization Methods, Euro. J. Mass Spectrom., 16:11-20.

Search Report and Written Opinion issued in counterpart PCT Application No. PCT/US2016/053610 dated Dec. 19, 2016.

Sokol, 2011, Miniature mass spectrometer equipped with electrospray and desorption electrospray ionization for direct analysis of organics from solids and solutions, Int. J. Mass Spectrum. 306:187-195.

Xu, 2010, Miniaturization of Mass Spectrometry Analysis Systems, JALA, vol. 15: pp. 433-439.

* cited by examiner 1 nM 10 nM

10 nM

100 nM

MASS TAG ANALYSIS FOR RARE CELLS AND CELL FREE MOLECULES

RELATED APPLICATION

The present application is a 35 U.S.C. § 371 national phase application of PCT/US2016/053610, filed Sep. 24, 2016, which claims the benefit of and priority to U.S. provisional application Ser. No. 62/222,940, filed Sep. 24, 2015, the content of each of which is incorporated by reference herein in its entirety.

FIELD OF THE INVENTION

The invention generally relates to mass tag analysis for rare cells and cell free molecules.

BACKGROUND

Cellular analysis is important in medical applications such as, for example, diagnosis of many diseases. The detection of rare molecules that are cell bound or included in the cell is also desirable. The medical applications of cellular analysis require isolation of certain cells of interest, which typically represent only a small fraction of a sample under analysis. For example, circulating tumor cells ("CTCs") are of particular interest in the diagnosis of metastatic cancers. In conventional methods, CTCs are isolated from whole blood by first removing red blood cells (RBCs) by lyses. In a 10 mL blood sample, a few hundred CTCs are to be separated from about 800,000,000 white blood cells ("WBCs"). Therefore, methods with high separation efficiency and cell recovery rates are necessary.

However, existing technologies are ineffective for detecting rare molecules from a sample. For example, the detection of rare molecules cannot be achieved by conventional affinity assays, which require a number of molecular copies far above the numbers found for rare molecules. The detection of rare molecules can be achieved by conventional nucleic acid assays. However, the target nucleic acids must be subjected to one or more lengthy purification steps and amplifications that can take several days for analysis time.

Cell filtration for the separation of rare cells using a porous matrix is a useful method used to sort cells by size and, in most instances, such filtration methods allow for the extraction of cells following separation. However, the existing filtration methods are limited by certain factors, which include, for example, the range of diameters that in vitro cells have rather than a single diameter. Additionally, cell filtration techniques yield only a few rare cells. The number of copies of a rare molecule can be significant at only tens of thousands of copies per cell for proteins or a few copies per cell for a gene mutation.

Rare cells can be analyzed down to the single cell level by a conventional scanning microscopy. However, even with automation of the scanning and analysis, the microscopy method can take 24 hours or more for each sample to be scanned. Additionally, all the rare cells with multiple images must be examined visually by the pathologist to determine the significance of protein amounts measured.

Mass spectroscopy (MS) has several issues that keep MS from being competitive with routine affinity reaction systems. The noted problems are inability to separate markers of interest from sample interference (matrix over lapping peaks), loss of sensitivity due to background in clinical sample (picomolar (pM) reduced to nanomolar (nM)), the inability to work with small nL sample volumes as samples less than 1 microliters (μl) are inefficiently captured for ionization and inefficiently isolated from interfering peaks in complex samples such as blood. In addition, MS often is not able to detect certain masses due to competition with other molecules of the same mass being ionized. These issues typically cause problems and provide false results.

SUMMARY

The invention recognizes that when mass spectral analysis is employed in carrying out rare target detection, it is important to avoid dilution of the detection liquid because dilution substantially reduces sensitivity of detection. Cells or capture particles in a detection liquid should be individually detected because each has a unique nature. Accordingly, the invention provides methods and apparatuses that provide for release of precise small amounts of detection liquid from a membrane and for delivery of liquid droplets into a mass spectrometer while avoiding dilution of the detection liquid.

Aspects of the invention are accomplished with an apparatus that includes an essentially non-absorbent membrane (non-bibulous membrane) including at least one pore, a microwell operably associated with the membrane, and an electric field generator operably associated with the membrane. A heterogeneous sample (e.g., a blood sample) is introduced to at least the microwell, the membrane, or both of the apparatus. A plurality of affinity agents are introduced to the sample. Each of the plurality of affinity agents includes a first molecule. The plurality of affinity agents specifically bind the target analyte in the sample. Unbound affinity agents are removed (e.g., by washing). One or more additional molecules are introduced to the sample. The one or more additional molecules interact with the first molecule to form a mass spectrometry label. A voltage is provided to the sample via the electric field generator in order to release a droplet through the at least one pore. The droplet includes a portion of the sample and the mass spectrometry label. The droplet is analyzed for presence of the mass spectrometry label, for example by mass spectrometry analysis of an ionized mass spectrometry label. The presence of the mass spectrometry label indicates presence of the target analyte in the sample. In certain embodiments, methods of the invention may additionally involve quantifying the target analyte in the sample by quantifying an amount of mass spectrometry label analyzed.

Generally, the at least one pore includes a proximal opening, a distal opening, and walls. Many different orientations of the pore are within the scope of the invention. For example, the walls of the at least one pore may oriented to be 90 degrees with respect to the proximal and distal openings. In another embodiment, the walls of the at least one pore taper from the proximal opening toward the distal opening. In another embodiment, the walls of the at least one pore taper from the distal opening toward the proximal opening.

In certain embodiments, the essentially non-absorbent membrane includes a plurality of pores. The plurality of pores may have the same dimensions. Alternatively, the plurality of pores may have different dimensions. In such embodiments, the apparatus is configured to generate an electric field from the electric field generator that produces a droplet from only one of the plurality of pores.

The apparatus may further include a mass spectrometer. The mass spectrometer may be a bench-top mass spectrometer or a miniature mass spectrometer, such as described for example in Gao et al. (Z. Anal. 15 Chem. 2006, 78, 5994-6002), Gao et al. (Anal. Chem., 80:7198-7205, 2008), Hou et al. (Anal. Chem., 83:1857-1861, 2011), Sokol et al. (Int. J. Mass Spectrom., 2011, 306, 187-195), Xu et al. (JALA, 2010, 15, 433-439); Ouyang et al. (Anal. Chem., 2009, 81, 2421-2425); Ouyang et al. (Ann. Rev. Anal. Chem., 2009, 2, 187-25 214); Sanders et al. (Euro. J. Mass Spectrom., 2009, 16, 11-20); Gao et al. (Anal. Chem., 2006, 78(17), 5994-6002); Mulligan et al. (Chem. Com., 2006, 1709-1711); and Fico et al. (Anal. Chem., 2007, 79, 8076-8082).), the content of each of which is incorporated herein by reference in its entirety.

In certain embodiments, the apparatus is configured such that the electric field generator inductively imparts the electric field to the sample in the microwell, such as described for example in U.S. Pat. No. 9,184,036, the content of which is incorporated by reference herein in its entirety.

In certain embodiments, the first molecule is a mass spectrometry label precursor. In such embodiments, the one or more additional molecules is an alteration agent that interacts with the mass spectrometry label precursor to form the mass spectrometry label.

In other embodiments, the first molecule is an alteration agent. In such embodiments, the one or more additional molecules is a mass spectrometry precursor label that interacts with the alteration agent to form the mass spectrometry label.

In certain embodiments, the first molecule is a mass spectrometry label precursor, and the one or more additional molecules are first and second alteration agents that interact with the mass spectrometry label precursor to form the mass spectrometry label.

The affinity agent may be a particulate or a non-particulate. The target analyte may be a rare cell and the heterogeneous sample may be a heterogeneous biological sample.

Some exemplary methods of the invention are directed to methods of releasing liquid from an essentially non-absorbent membrane including at least one pore. The essentially non-absorbent membrane may be associated with a microwell that is capable of holding liquid. An intersection of the at least one pore and at least one surface of the essentially non-absorbent membrane is at an angle of about 30° to about 150°. The method may involve exposing the liquid on the essentially non-absorbent membrane to an electrical field to release one or more droplets of the liquid through the at least one pore of the essentially non-absorbent membrane.

Other exemplary methods involve detecting one or more different populations of target rare molecules in a sample suspected of containing the one or more different populations of rare molecules and non-rare molecules. A sample (typically in liquid form), may be contacted to an apparatus that involves a microwell and an essentially non-absorbent membrane having at least one pore. The intersection of the at least one pore and at least one surface of the essentially non-absorbent membrane is at an angle of about 30° to about 150°. The sample may be incubated with, for each different population of target rare molecules, an affinity agent that includes a binding partner that is specific for and binds to a target rare molecule of one of the populations of the target rare molecules. The affinity agent includes a mass spectrometry label precursor or a first alteration agent. The affinity agent may be non-particulate or particulate. The first alteration agent either facilitates the formation of a mass spectrometry label from the mass spectrometry label precursor or releases an entity that includes the mass spectrometry label precursor from the affinity agent. If the first alteration agent does not facilitate the formation of a mass spectrometry label from the mass spectrometry label precursor, the sample is subjected to a second alteration agent that facilitates the formation of a mass spectrometry label from the mass spectrometry label precursor. The mass spectrometry label corresponds to one of the populations of target rare molecules. The sample on the essentially non-absorbent membrane is exposed to an electrical field to release one or more droplets of the sample through the at least one pore of the essentially non-absorbent membrane. The droplets are subjected to mass spectrometry analysis to determine the presence and/or amount of each different mass spectrometry label. The presence and/or amount of each different mass spectrometry label may be correlated to the presence and/or amount of each different population of target rare molecules in the sample for each microwell.

In other aspects, the invention provides sample analysis methods that involve introducing a sample suspected of comprising a target analyte to a membrane that includes a pore (e.g., an essentially non-absorbent membrane but optionally an absorbent membrane). One or more reagents are introduced to the sample on the membrane to generate a mass spectrometry label associated with target analyte if present in the sample. An electric field is applied to the membrane to thereby generate one or more droplets of the sample that are expelled from the pore of the membrane and are introduced into a mass spectrometer. A presence of the target analyte is detected via the mass spectrometer by detecting a presence of the mass spectrometry label. A portion of the sample associated with the pore of the membrane is then extracted from the membrane if the target analyte is present based on results from the detecting step, and the extracted portion of the sample is analyzed. The methods of the invention may further involve quantifying the target analyte in the sample by quantifying an amount of mass spectrometry label analyzed.

The introduction of one or more reagents to the sample on the membrane may involve introducing to the sample a plurality of affinity agents that each include a first molecule, wherein the plurality of affinity agents specifically bind the target analyte in the sample, removing unbound affinity agents, and introducing one or more additional molecules to the sample, wherein the one or more additional molecules interact with the first molecule to form a mass spectrometry label.

In certain embodiments, the first molecule is a mass spectrometry label precursor. In such embodiments, the one or more additional molecules is an alteration agent that interacts with the mass spectrometry label precursor to form the mass spectrometry label.

In other embodiments, the first molecule is an alteration agent. In such embodiments, the one or more additional molecules is a mass spectrometry precursor label that interacts with the alteration agent to form the mass spectrometry label.

In other embodiments, the first molecule is a mass spectrometry label precursor, and the one or more additional molecules are first and second alteration agents that interact with the mass spectrometry label precursor to form the mass spectrometry label.

In all of these embodiments, the affinity agent may be a particulate or a non-particulate. In exemplary embodiments, the target analyte is a rare cell and the sample is a heterogeneous biological sample.

DETAILED DESCRIPTION

Figure 1A:
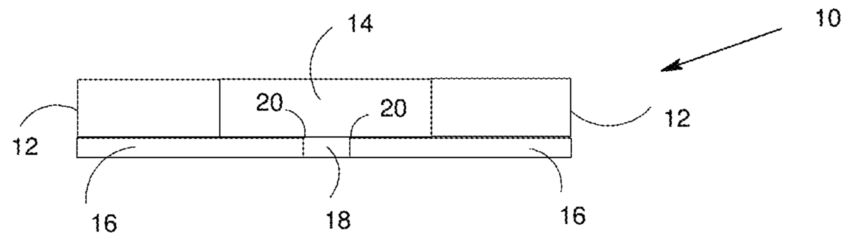
FIGS. 1A-C are schematics depicting examples of apparatuses of the invention having different pore orientations.

The invention generally relates to methods and apparatus for releasing liquid from a membrane especially in the area of analysis of small amounts (on the microliter (μL) scale or less) of liquids that contain only a few molecules (on the femtomolar (fM) scale or less). In some aspects, the invention relates to methods, apparatuses and kits for detecting one or more different populations of rare molecules in a biological sample (e.g., blood sample) suspected of containing the one or more different populations of rare molecules and non-rare molecules. In some aspects, the invention relates to methods and kits for detecting one or more different populations of rare molecules that are freely circulating in a biological sample (e.g., blood). In other aspects, the invention relates to methods and kits for detecting one or more different populations of rare molecules that are associated with rare cells in a biological sample (e.g., blood sample) suspected of containing the one or more different populations of rare cells and non-rare cells.

Methods of the invention for detecting one or more different populations of target rare molecules in a sample may involve enhancing the concentration of the one or more different populations of target rare molecules over that of the non-rare molecules. A concentrated sample is formed and is incubated with, for each different population of target rare molecules, an affinity agent that comprises a binding partner that is specific for and binds to a target rare molecule of one of the populations of the target rare molecules. The affinity agent may be non-particulate or particulate. The affinity agent comprises a mass spectrometry (MS) label precursor or a first alteration agent, which either facilitates the formation of an MS label from the MS label precursor or releases an entity that comprises the MS label precursor from the affinity agent. The MS label corresponds to one of the populations of target rare molecules. A retentate and a filtrate are formed by contacting the incubated sample with a porous matrix. One or both of the retentate and the filtrate are subjected to a second alteration agent that facilitates the formation of a MS label from the MS label precursor from the affinity agent if the first alteration agent does not facilitate the formation of a MS label from the MS label precursor. One or both of the retentate and the filtrate are subjected to MS analysis to determine the presence and/or amount of each different MS label. The presence and/or amount of each different MS label are related to the presence and/or amount of each different population of target rare molecules in the sample.

In another example, a ratio of rare cells to non-rare cells in a blood sample suspected of containing rare cells and non-rare cells is increased. A treated blood sample is prepared by providing in combination the blood sample, a platelet deactivation agent, a fibrin-formation-arresting agent and fibrin in an amount sufficient to cause a predetermined level of agglutination of the rare cells. The treated blood sample is then contacted with a porous matrix such that agglutinated rare cells are preferentially retained on the porous matrix.

In another example, methods of separating rare cells with intact nucleic acids from non-rare cells in a sample comprising the rare cells and non-rare cells are employed. The sample is combined with an aqueous medium, and the combination is held for a period of time and at a temperature for selectively releasing nucleic acids from the non-rare cells but not from the rare cells. The sample is subjected to filtration to separate rare cells from non-rare cells.

General Discussion

The apparatuses described herein permit formation of ionized droplets from a small quantity of liquid that is retained on an essentially non-absorbent membrane and further permits the subsequent release of the droplets from the essentially non-absorbent membrane through at least one pore of the essentially non-absorbent membrane (non-bibulous membrane).

An example of an apparatus of the invention is depicted in FIG. 1. Apparatus 10 comprises circular wall 12 having microwell 14 and essentially non-absorbent membrane 16 with at least one pore 18. Pore 18 and essentially non-absorbent membrane 16 intersect at point 20 at an angle of 90°. The pore acts to facilitate generation and release of droplets (e.g., liquid droplets) from the apparatus 10.

Figure 2:
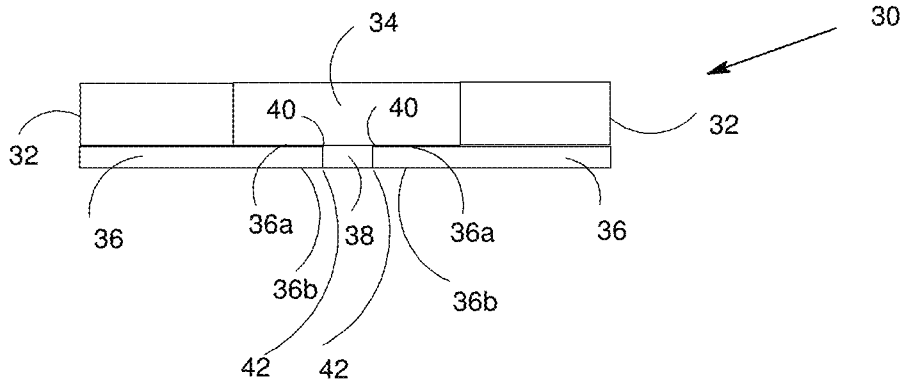
FIG. 2 is a schematic depicting another example of an apparatus in accordance with the invention.

Another example of an apparatus of the invention is depicted in FIG. 2. Apparatus 30 comprises circular wall 32 having microwell 34 and essentially non-absorbent membrane 36 with at least one pore 38. Upper surface **36*a* of membrane 36 and inner surface 38*a* of pore 38 intersect at point 40 at an angle of 90° and lower surface 36*b* of membrane 36 and inner surface 38*a* of pore 38 intersect at point 42 at an angle of 90°. The pore acts to facilitate generation and release of droplets (e.g., liquid droplets) from the apparatus 30**.

Figure 3:
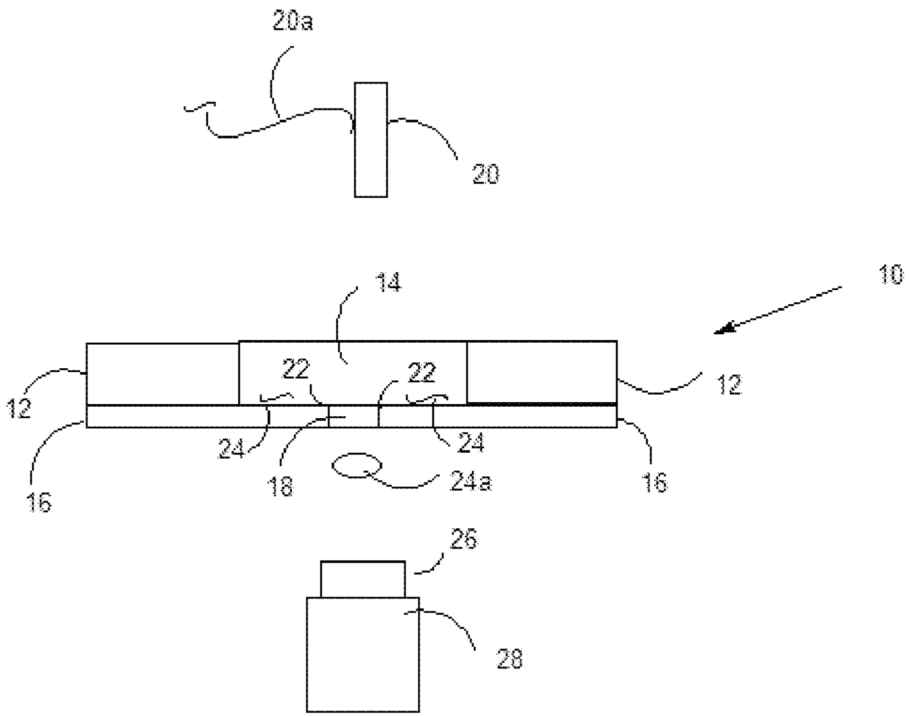
FIG. 3 is a schematic depicting an example of an apparatus and method of the invention for releasing a liquid droplet from the apparatus shown in FIG. 1, which droplet enters an intake of a mass spectrometer.

FIG. 3 depicts an example of releasing a droplet (e.g., liquid droplet) from an apparatus as described in FIG. 1. Liquid 24 is contained in microwell 14 and does not have sufficient volume to pass through pore 18 of essentially non-absorbent membrane 16. Electric field generator 20 is activated by wire **20*a* to produce an electric field having sufficient intensity to result in the release of droplet 24*a* from essentially non-absorbent membrane 16 through pore 18. Droplet 24*a* is collected in inlet 26 of mass spectrometer 28**.

Mass spectrometer 28 can be any type of mass spectrometer known in the art, such as a bench-top mass spectrometer or a miniature mass spectrometer. An exemplary miniature mass spectrometer is described, for example in Gao et al. (Z. Anal. Chem. 2006, 78, 5994-6002), the content of which is incorporated by reference herein in its entirety In comparison with the pumping system used for lab-scale instruments with thousands watts of power, miniature mass spectrometers generally have smaller pumping systems, such as a 18 W pumping system with only a 5 L/min (0.3 m3/hr) diaphragm pump and a 11 L/s turbo pump for the system described in Gao et al. Other exemplary miniature mass spectrometers are described for example in Gao et al. (Anal. Chem., 80:7198-7205, 2008), Hou et al. (Anal. Chem., 83:1857-1861, 2011), and Sokol et al. (Int. J. Mass Spectrom., 2011, 306, 187-195), the content of each of which is incorporated herein by reference in its entirety. Miniature mass spectrometers are also described, for example in Xu et al. (JALA, 2010, 15, 433-439); Ouyang et al. (Anal. Chem., 2009, 81, 2421-2425); Ouyang et al. (Ann. Rev. Anal. Chem., 2009, 2, 187-214); Sanders et al. (Euro. J. Mass Spectrom., 2009, 16, 11-20); Gao et al. (Anal. Chem., 2006, 78(17), 5994-6002); Mulligan et al. (Chem. Com., 2006, 1709-1711); and Fico et al. (Anal. Chem., 2007, 79, 8076-8082).), the content of each of which is incorporated herein by reference in its entirety.

Figure 4:
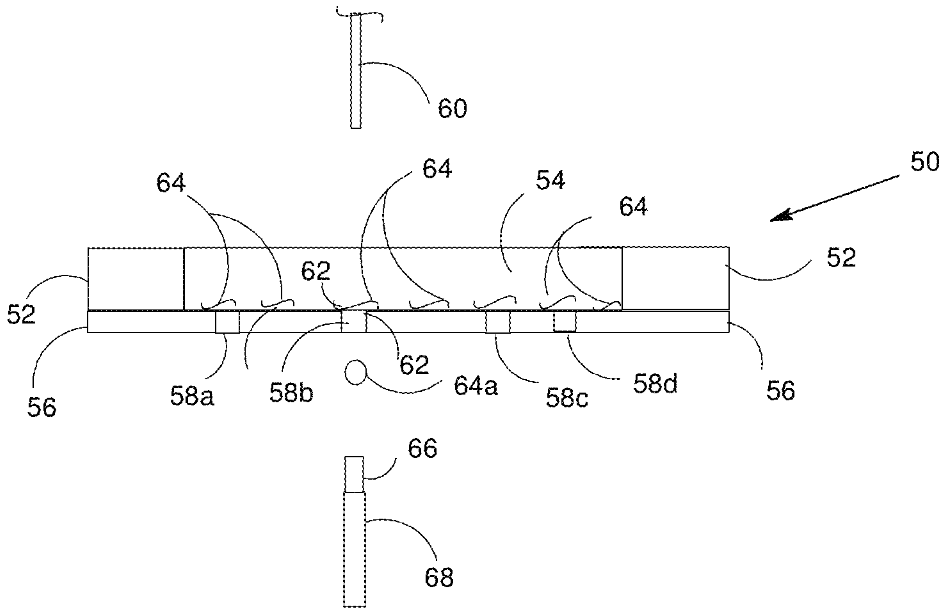
FIG. 4 is a schematic depicting an example of an apparatus and method of the invention having more than one pore. A droplet released from one of the pores enters an intake of a mass spectrometer.

FIG. 4 depicts another example of an apparatus of the invention that includes an array of pores. Liquid 64 is contained in microwell 54 of apparatus 50 and does not have sufficient volume to pass through pores 58*a*-58*d* of essentially non-absorbent membrane 56. Microwell 54 has circular wall 56. Electric field generator 60 is activated to produce an electric field having sufficient intensity to result in the release of droplet 64*a* from essentially non-absorbent membrane 56 only through individual pore 58*b*. Droplet 64*a* is collected in inlet 66 of mass spectrometer 68. In this example, the dimensions of the electric field generator are selected to apply an electrical field precisely to a single pore or to a subset of pores. Thus, the electrical field generator is designed accordingly so that the electrical field generator includes at least a portion (such as, e.g., a tip, wire, needle, cone, rectangle, or sphere) that permits such an application. In this example, the dimensions of the electrical field generator at the point of application of the electrical field should be about the size of the pore or the subset of pores to which selective application of the electrical field is desired. Thus, the dimensions of the electrical field generator at the point of application of the electrical field should be no greater than about 200% and no less than about 50%, or no greater than about 150% and no less than about 25%, or no greater than about 100% and no less than about 50%, or no greater than about 50% and no less than about 25%, of the size of the pore or the subset of pores. Furthermore, the inlet of a mass spectrometer should be aligned with the electrical field generator. In some examples, the inlet of the mass spectrometer has dimensions that correspond with that of the electrical field generator at the point of application of the electrical field.

Figure 5:
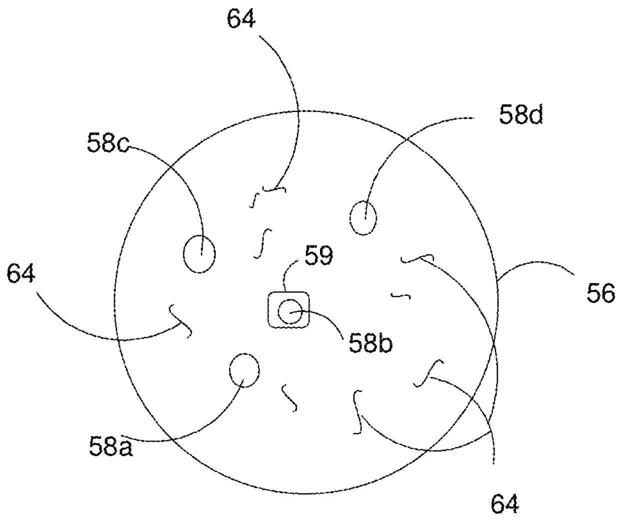
FIG. 5 depicts the essentially non-absorbent membrane of the apparatus of FIG. 4 in which an area on the essentially non-absorbent membrane is identified for further analysis.

Referring to FIGS. 4 and 5, an MS label in droplet 64*a* is identified as a result of MS analysis and a corresponding area 59 on essentially non-absorbent membrane 56 is selected for further analysis. Liquid or particle (including cell) is removed from area 59 by suction, punching out, dissection, or extraction, for example, or a combination of two or more of the above.

In the apparatuses described above, the essentially non-absorbent membrane may be a flat surface that is essentially or completely impermeable to the liquid. The essentially non-absorbent membrane includes at least one pore, and in certain embodiments more than one pore (e.g., an array of pores). The at least one pore has a fixed orientation within the essentially non-absorbent membrane. That fixed orientation may be described with respect to how the walls of the pore intersect the surface of the essentially non-absorbent membrane. For example, the pore can have vertical walls such that the walls of the pore intersect the surfaces (top surface that faces the microwell (proximal surface) and bottom surfaces that faces the mass spectrometer (distal surface)) of the essentially non-absorbent membrane at 90 degrees. Such an orientation of the pore is shown in FIG. 1A.

Figure 1B:
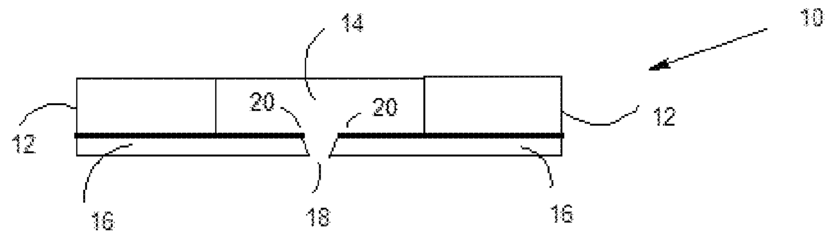
Figure 1C:
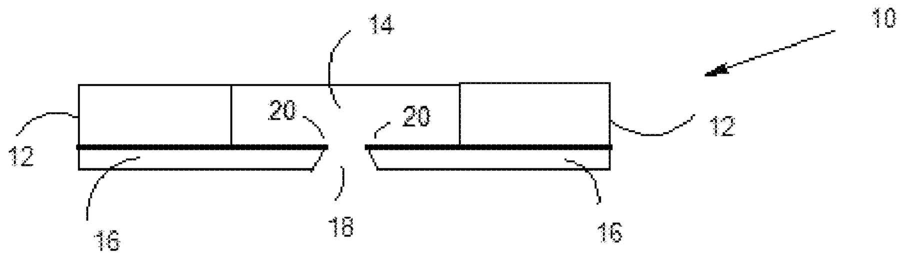

Other orientations are possible and the skilled artisan will appreciate that the invention is not limited to a specific orientation of the pore. For example, the walls of the pore can intersect the surfaces of the essentially non-absorbent membrane at an angle at the intersection of the two surfaces of about 30° to about 150°. That allows for the pore to taper from the proximal surface toward the distal surface as shown in FIG. 1B (i.e., the pore is dimensioned to become more narrow). Alternatively, the pore can taper from the distal surface to the proximal surface FIG. 1C (i.e., the pore is dimensioned to become broader). In some examples where the essentially non-absorbent membrane comprises more than one pore, the angle at the intersection has a high degree of precision (less than 1 degree of variability) from one pore to another, i.e., the pores all have the same dimensions. Thus, in this example, an angle of a pore and a surface of the essentially non-absorbent membrane does not differ from an angle of another pore by more than 1°. In other embodiments, the some or all of the pores have different dimensions from each other.

The term "intersection" means the point or series of points where two surfaces touch one another. In some examples where the essentially non-absorbent membrane comprises more than one pore, an angle of one of the pores and a surface of the essentially non-absorbent membrane does not differ from an angle of another pore by more than 1°, or by more than 0.5°, or by 0.2°, or by more than 0.1°, or by more 0.05°, or by more than 0.01°, or by more than 0.005°, or by more than or by more than 0.001°, for example.

In some examples, the liquid on the essentially non-absorbent membrane is exposed to an electrical field to cause release of one or more liquid droplets from the essentially non-absorbent membrane. The electric field can also cause ionization of molecules within the droplets. The essentially non-absorbent membrane is also associated with an electrical field generator. Activation of the electrical field generator produces an electrical field, which causes liquid to more through the pore and form a liquid droplets that is released from the membrane through the at least one pore into, for example, an inlet of a mass spectrometer.

As mentioned above, the essentially non-absorbent membrane is associated with a microwell capable of holding liquid. The phrase "associated with" means that the essentially non-absorbent membrane and the microwell may form a single unit in which the essentially non-absorbent membrane may be on the bottom of the microwell or on the top of the microwell.

The liquid may be the sample or a liquid that contains an MS label. The liquid may also be the MS label that is introduced to the sample. In some examples, the liquid comprises a solvent such as, for example, a spray solvent employed in electrospray mass spectroscopy. In some examples, solvents for electrospray ionization include, but are not limited to, polar organic compounds such as, e.g., alcohols (e.g., methanol, ethanol and propanol), acetonitrile, dichloromethane, dichloroethane, tetrahydrofuran, dimethylformamide, dimethylsulphoxide, and nitromethane; non-polar organic compounds such as, e.g., hexane, toluene, cyclohexane; and water, for example, or combinations of two or more thereof. Optionally, the solvents may contain one or more of an acid or a base as a modifier (such as, volatile salts and buffer, e.g., ammonium acetate, ammonium biocarbonate, volatile acids such as formic acid, acetic acids or trifluoroacetic acid, heptafluorobutyric acid, sodium dodecyl sulphate, ethylenediamine tetraacetic acid, and non-volatile salts or buffers such as, e.g., chlorides and phosphates of sodium and potassium, for example.

The membrane is essentially non-absorbent, which means that the membrane is essentially incapable of absorbing liquid (non-bibulous). In some examples, the amount of liquid absorbed by the essentially non-absorbent membrane is less than about 2% (by volume), or less than about 1%, or less than about 0.5%, or less than about 0.1%, or less than about 0.01%, or 0%. The essentially non-absorbent membrane may be non-fibrous, which means that the membrane is at least 95% free of fibers, or at least 99% free of fibers, or at least 99.5%, or at least 99.9% free of fibers, or 100% free of fibers.

The essentially non-absorbent membrane can be a solid, non-flexible material, which is impermeable to liquid (except through one or more pores of the membrane). The essentially non-absorbent membrane may be comprised of an organic or inorganic material or a water insoluble material. The shape of the essentially non-absorbent membrane is dependent on one or more of the nature of a holder or retainer for the essentially non-absorbent membrane, the nature and shape of the pore, the angle of the pore and the essentially non-absorbent membrane, the nature of the micro well, the nature of the charge generation, and the nature of a mass label, for example. In some examples the shape of the essentially non-absorbent membrane is circular, oval, rectangular, square, hexagonal, planar or flat surface (e.g., strip, disk, film, membrane, and plate), for example. In some examples the essentially non-absorbent membrane is rigid or non-flexible, which means that the essentially non-absorbent membrane may be flexed no more than about 1°, or no more than about 0.5°, or no more than about 0.1° from a plane of the essentially non-absorbent membrane.

The essentially non-absorbent membrane may be fabricated from a wide variety of materials, which may be naturally occurring or synthetic, polymeric or non-polymeric. Examples, by way of illustration and not limitation, of such materials for fabricating an essentially non-absorbent membrane include plastics such as, for example, polycarbonate, poly (vinyl chloride), polyacrylamide, polyacrylate, polyethylene, polypropylene, poly-(4-methylbutene), polystyrene, polymethacrylate, poly(ethylene terephthalate), nylon, poly(vinyl butyrate), poly(chlorotrifluoroethylene), poly(vinyl butyrate), polyimide, polyurethane, and paraylene; silanes; silicon; silicon nitride; graphite; ceramic material (such, e.g., as alumina, zirconia, PZT, silicon carbide, aluminum nitride); metallic material (such as, e.g., gold, tantalum, tungsten, platinum, and aluminum); glass (such as, e.g., borosilicate, soda lime glass, and PYREX (low-thermal-expansion borosilicate glass, Corning Incorporated)); and bioresorbable polymers (such as, e.g., poly-lactic acid, polycaprolactone and polyglycoic acid); for example, either used by themselves or in conjunction with one another and/or with other materials. The material for fabrication of the essentially non-absorbent membrane does not include fibrous materials such as cellulose (including paper), nitrocellulose, cellulose acetate, rayon, diacetate, lignins, mineral fibers, fibrous proteins, collagens, synthetic fibers (such as nylons, dacron, olefin, acrylic, polyester fibers, for example) or, other fibrous materials (glass fiber, metallic fibers), which are bibulous and/or permeable and, thus, are not in accordance with the principles described herein.

The essentially non-absorbent membrane for each microwell comprises at least one pore. The essentially non-absorbent membrane can include more than one pore, such as about 2,000,000 pores per square centimeter ($cm^2$). In some examples the number of pores of the essentially non-absorbent membrane per $cm^2$ is 1 to about 2,000,000, or 1 to about 1,000,000, or 1 to about 500,000, or 1 to about 200,000, or 1 to about 100,000, or 1 to about 50,000, or 1 to about 25,000, or 1 to about 10,000, or 1 to about 5,000, or 1 to about 1,000, or 1 to about 500, or 1 to about 200, or 1 to about 100, or 1 to about 50, or 1 to about 20, or 1 to about 10, or 2 to about 500,000, or 2 to about 200,000, or 2 to about 100,000, or 2 to about 50,000, or 2 to about 25,000, or 2 to about 10,000, or 2 to about 5,000, or 2 to about 1,000, or 2 to about 500, or 2 to about 200, or 2 to about 100, or 2 to about 50, or 2 to about 20, or 2 to about 10, or 5 to about 200,000, or 5 to about 100,000, or 5 to about 50,000, or 5 to about 25,000, or 5 to about 10,000, or 5 to about 5,000, or 5 to about 1,000, or 5 to about 500, or 5 to about 200, or 5 to about 100, or 5 to about 50, or 5 to about 20, or 5 to about 10, for example. The density of pores in the essentially non-absorbent membrane is about 1% to about 20%, or about 1% to about 10%, or about 1% to about 5%, or about 5% to about 20%, or about 5% to about 10%, for example, of the surface area of the essentially non-absorbent membrane. In some examples, the size of the pores of an essentially non-absorbent membrane is that which is sufficient to preferentially retain liquid while allowing the passage of liquid droplets formed in as described herein. The size of the pores of the essentially non-absorbent membrane is dependent on the nature of the liquid, the size of the cell, the size of the capture particle, the size of mass label, the size of an analyte, the size of label particles, the size of non-rare molecules, and the size of non-rare cells, for example. In some examples the average size of the pores of the essentially non-absorbent membrane is about 0.1 to about 20 microns, or about 0.1 to about 5 microns, or about 0.1 to about 1 micron, or about 1 to about 20 microns, or about 1 to about 5 microns, or about 1 to about 2 microns, or about 5 to about 20 microns, or about 5 to about 10 microns, for example.

As mentioned above, the intersection of a top and/or a bottom surface of the essentially non-absorbent membrane and an inner wall of a pore has an angle of about 30° to about 150°, or about 30° to about 125°, or about 30° to about 110°, or about 30° to about 100°, or about 30° to about 95°, or about 30° to about 90°, or about 45° to about 150°, or about 60° to about 150°, or about 75° to about 150°, or about 80° to about 150°, or about 85° to about 150°, or about 90° to about 150°, or about 45° to about 125°, or about 60° to about 110°, or about 70° to about 100°, or about 80° to about 100°, or about 85° to about 95°, or about 90°, for example. The intersection of the surfaces depends on the shape of each of the surfaces such as, for example, the pore, and may be linear, circular, oval, hexagonal, square, or rectangular, for example, or a combination thereof.

The above characteristics of membranes allow a high level of precision in an amount of liquid released as droplets from the membrane. The variation (CV) in an amount of liquid in droplets may be no more than about 1% (volume/volume), or no more than about 0.5%, or no more than about 0.1%, for example. Furthermore, the time at which the mass desorption from the solvent occurs (desorption time) is less variable, i.e., variable by no more than about 500 millisecond(s) (msec), or no more than about 400 msec, or no more than about 300 msec, or no more than about 200 msec, or no more than about 100 msec, or no more than about 50 msec, or no more than about 10 msec, thereby making the trapping of ions much more facile at short time, thus permitting smaller spray volumes in comparison to known methods. Desorption time is decreased further for rigid essentially non-absorbent membranes. In addition, shorter desorption times on the order of 50 msec may be realized where the essentially non-absorbent membrane comprises more than one pore and the angle for one pore at a surface of the essentially non-absorbent membrane does not differ from an angle for another pore by more than 0.5°. The precision obtained with apparatuses described herein allows for highly quantitative results. The phrase "mass desorption" refers to the separation of mass label ions from solvent molecules.

Microwells and membranes with pores may be fabricated by, for example, microelectromechanical (MEMS) technology, metal oxide semiconductor (CMOS) technology, micro-manufacturing processes for producing microsieves, laser technology, irradiation, molding, and micromachining, for example, or a combination thereof.

As mentioned above, the emission of analyte (or mass tag) containing charged droplets and analyte ions from pores of the essentially non-absorbent membrane (non-bibulous membrane) is accomplished by the generation of an electric field in the vicinity of the membrane. The electric field is established by providing an electrical potential of about 1 kilovolt (kV) to about 10 kilovolts (kV), or about 1 kV to about 5 kV, or about 2 kV to about 10 kV, or about 5 kV to about 10 kV, or about 6.0 to 6.5 kV to a conductive element (hereafter referred to as the electric field generator) located 0.05 mm up to 20 mm distant from the essentially non-absorbent membrane. The apparatus is typically positioned a distance of 0.01 mm to 5 mm from the inlet capillary of a mass spectrometer, which may be held at a potential of −300 V up to +300 V.

The nature and intensity of the electric field is dependent on one or more of the following: the nature of the liquid, the pore size, the amount of spray liquid, the distance between the membrane and the electric field generator, the distance between the membrane and the inlet of the mass spectrometer, and the potentials applied to the electric field generator and the inlet of the mass spectrometer. In some cases the electrical potential is supplied continuously via a high voltage source in order to generate a continuous spray from the membrane. In other cases, the electrical potential is supplied by compressing or decompressing a piezo-electric device (such as an anti-static gun) that is connected to the electric field generator. Furthermore, discrete emission of charged droplets and analytes from the membrane may be accomplished by providing one, or a series of electrical pulses in the range of 1 kV to about 15 kV, to the electric field generator for a duration from as little as 0.5 ms per individual pulse to as much as 2 minutes per individual pulse.

The volume of liquid expelled through the pore or the subset of pores is dependent on the volume of the samples, the size of the pore, nature of analysis, size of the well, the number of pores in a well, the number of wells in the generated filed, the number of pores in the generated field, the pore size, the pore angle, and the rigidity of the membrane, for example. In some examples, the volume of liquid expelled is about 1 fL to about 1 μL, or about 1 nL to about 1 μL, for example.

In some examples, an electrical field generator is associated with the essentially non-absorbent membrane and is activated to produce an electrical field. In some examples the electrical field generator is an electrical grid line integral with a support for the essentially non-absorbent membrane. In some examples the electrical field generator is an electrical grid separate from the essentially non-absorbent membrane and is disposed for movement to and from the essentially non-absorbent membrane. In some examples one or both of the electrical field generator and the essentially non-absorbent membrane are attached to a robotic arm that is capable of movement to bring the electrical field generator into disposition with respect to the essentially non-absorbent membrane to permit activation of the electrical field generator to selectively induce droplet formation on an area of the essentially non-absorbent membrane or on a particular essentially non-absorbent membrane or group of essentially non-absorbent membranes where the essentially non-absorbent membrane may be part of an array of essentially non-absorbent membranes as discussed below.

In some examples of the electrical field generator is a line, a plate, an ion stream or combinations thereof. Application of, for example, an electrical potential, to the electrical field generator results in activation of the electrical field generator. An ion stream may be produced by different means including, but not limited to the generation of a plasma by dielectric barrier discharge, the application of an alternating electrical potential to a suitable conductive element, the application of a static electrical potential to a suitable conductive element, or the compression of a piezoelectric material which is connected to a suitable conductive element. In each case, the suitable conductive element is composed of an electrical conductive material of suitable geometry such that the electric field strength (upon application of electrical potential) is of sufficient magnitude to cause electrical breakdown of the surrounding medium. In some cases this suitable conductive element may be a wire, a protrusion or series of protrusions, a plate, a grid or mesh, a pointed rod, or a roughened surface. An ion stream may also be produced by electrospraying a suitable liquid. The generated ion stream is directed at one side of the non-bibulous membrane while the opposite side of the membrane is positioned near the inlet of a mass spectrometer as described previously. The ion stream may be directed by, but is not limited to, positioning the ion stream generator in an appropriate manner such that the ion stream travels toward and impinges on the non-bibulous membrane, providing suitable electrical potentials to a series of conductive electrodes to electrostatically direct ions toward the membrane, or through the use of pneumatic forces—such as a flowing gas—to carry the ion stream towards the membrane. Inductively charging and inductive ionization of a sample may also be used and are described further below and for example in U.S. Pat. No. 9,184,036, the content of which is incorporated by reference herein in its entirety.

The essentially non-absorbent membrane may be associated with a housing, which may be the microwell, in which the essentially non-absorbent membrane may be positioned, for example, at a top or a bottom of the housing. The housing may be constructed of any suitable material that is compatible with the material of the essentially non-absorbent membrane. Examples of such materials include, by way of example and not limitation, any of the materials listed above for the essentially non-absorbent membrane. The material for the housing and for the essentially non-absorbent membrane may be the same or may be different. In some examples, the essentially non-absorbent membrane is part of a microwell.

As mentioned above, in some examples the essentially non-absorbent membrane is part of a microwell or an array of microwells. The essentially non-absorbent membranes of at least two of the microwells may comprise liquid samples, which may be the same or different, and the electrical field may be activated to selectively release droplets from each of the essentially non-absorbent membranes of the at least two microwells. The top or the bottom of the microwell may comprise the essentially non-absorbent membrane. The volume of the microwell is dependent on the nature of the liquid samples, the nature of the pore, the nature and size of the essentially non-absorbent membrane, the spray solvent, the capture particle or cell, the analyte concentrations, the mass label concentration, for example. In some examples the volume of the microwell is about 1 femtoliter(s) (fL) to about 100 microliters (μL), or about 1 μL to about 100 nanoliters (nL), or about 1 μL to about 50 nL, or about 1 μL to about 10 nL, or about 1 μL to about 5 nL, or about 1 μL to about 1 nL, or about 1 nL to about 2 nL. In some examples, where the microwells are circular, the diameter of the microwell is about 5 micrometers (μm) to about 40 millimeters (mm), or about 5 μm to about 500 μm, or about 500 μm to about 2 mm, or about 2 mm to about 40 mm. The microwell around a single pore can hold a defined volume of liquid, which allows a defined spray liquid volume and therefore a fixed high concentration of an analyte and short desorption time of the liquid within the pore.

The array can comprise 2 to about 100,000 microwells, or 2 to about 50,000 microwells, or 2 to about 10,000 microwells, or 2 to about 5,000 microwells, or 2 to about 2,500 microwells, or 2 to about 1,000 microwells, or 2 to about 500 microwells, or 2 to about 100 microwells, or 2 to about 50 microwells, or about 10 to about 100,000 microwells, or about 10 to about 50,000 microwells, or about 10 to about 10,000 microwells, or about 10 to about 5,000 microwells, or about 10 to about 2,500 microwells, or about 10 to about 1,000 microwells, or about 100 to about 10,000 microwells, or about 100 to about 5,000 microwells, or about 100 to about 2,500 microwells, or about 5,000 to about 10,000 microwells, or about 2,500 to about 7,500 microwells, for example.

An array of apparatus 10 in an example in accordance with the principles described herein is depicted in FIG. 5. Array 70 is shown comprising 24×32 grid (768) of apparatus 10, each comprising a microwell 14.

Figure 6:
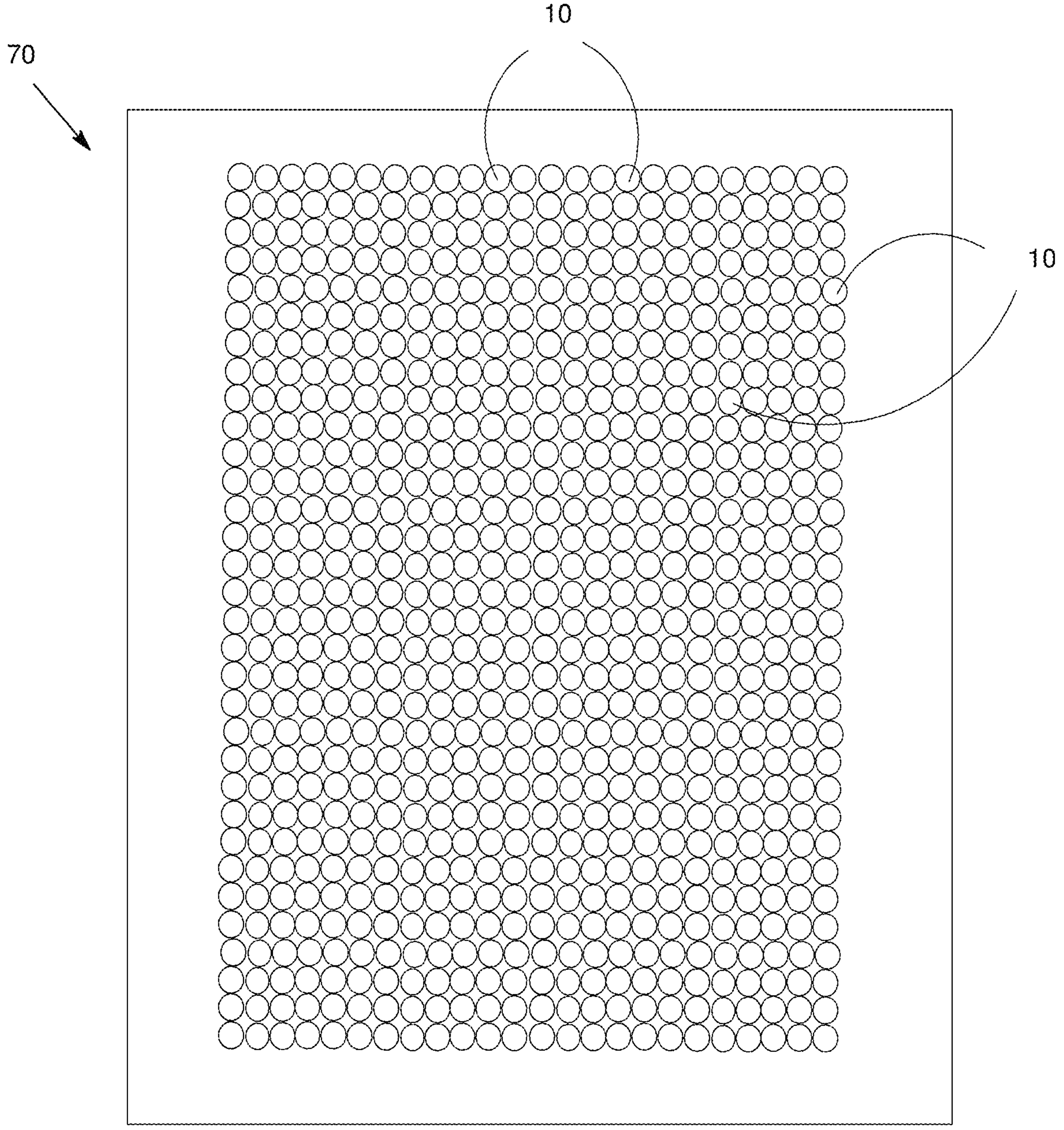
FIG. 6 is a schematic depicting an example of a microwell array.
Figure 7:
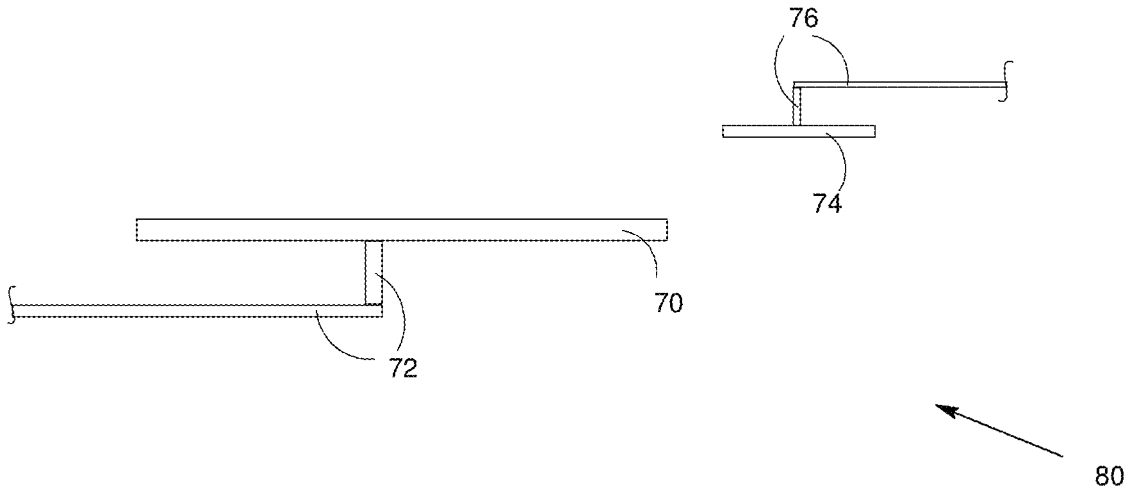
FIG. 7 is a schematic depicting an example of an apparatus including an array and an electric field generator.
Figure 8A:
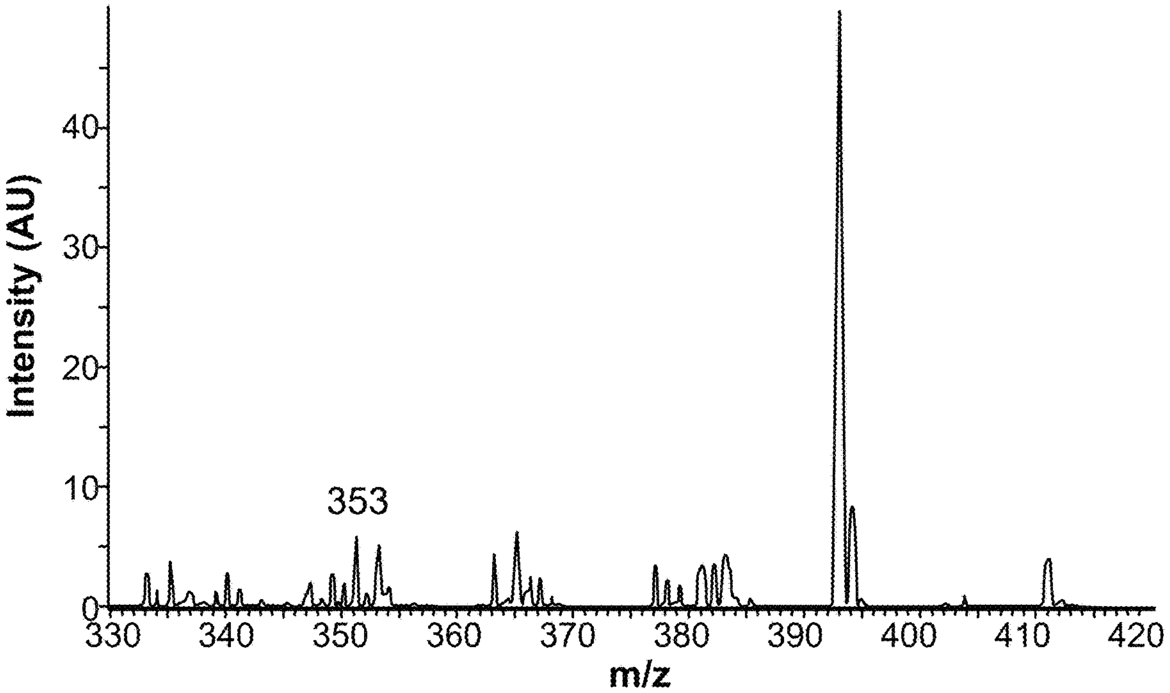
FIGS. 8A-C are a set of mass spectra showing FC-2 peptide sprayed directly from an apparatus of the invention. The set of mass spectra are MS/MS spectra for m/z 412 generated from the peptide FC-2 at various concentrations.
Figure 8B:
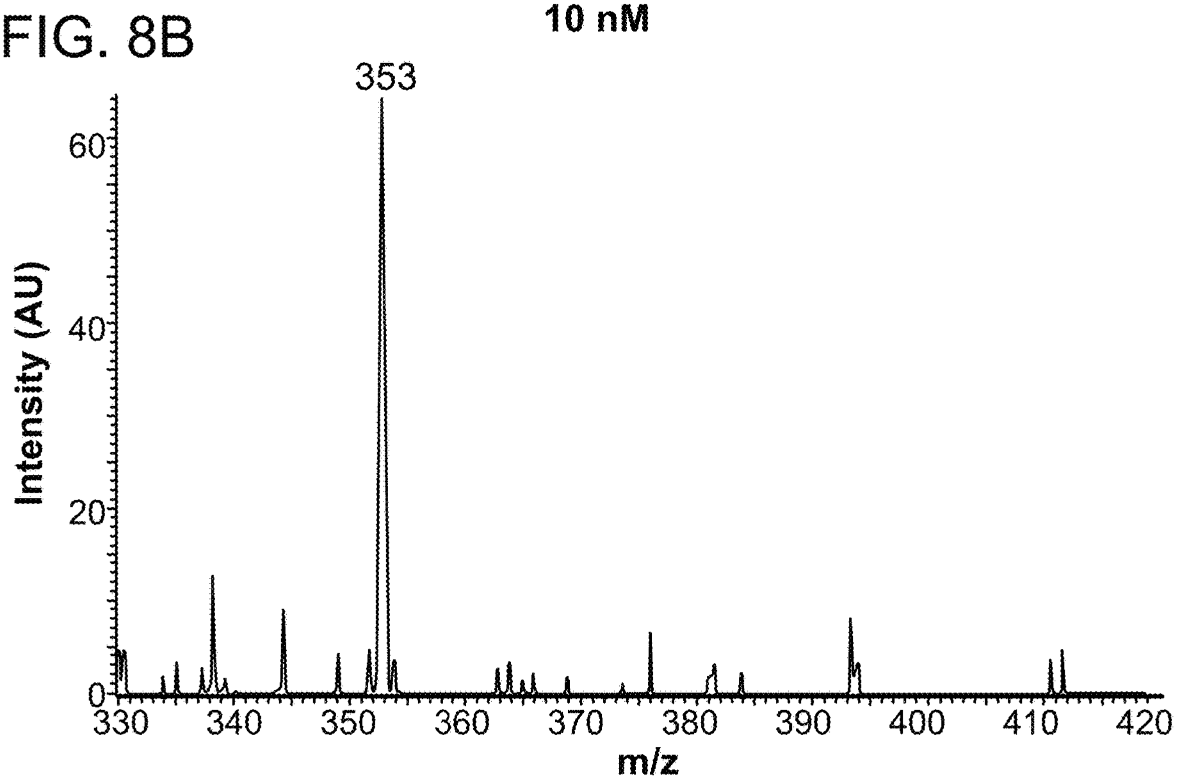
Figure 8C:
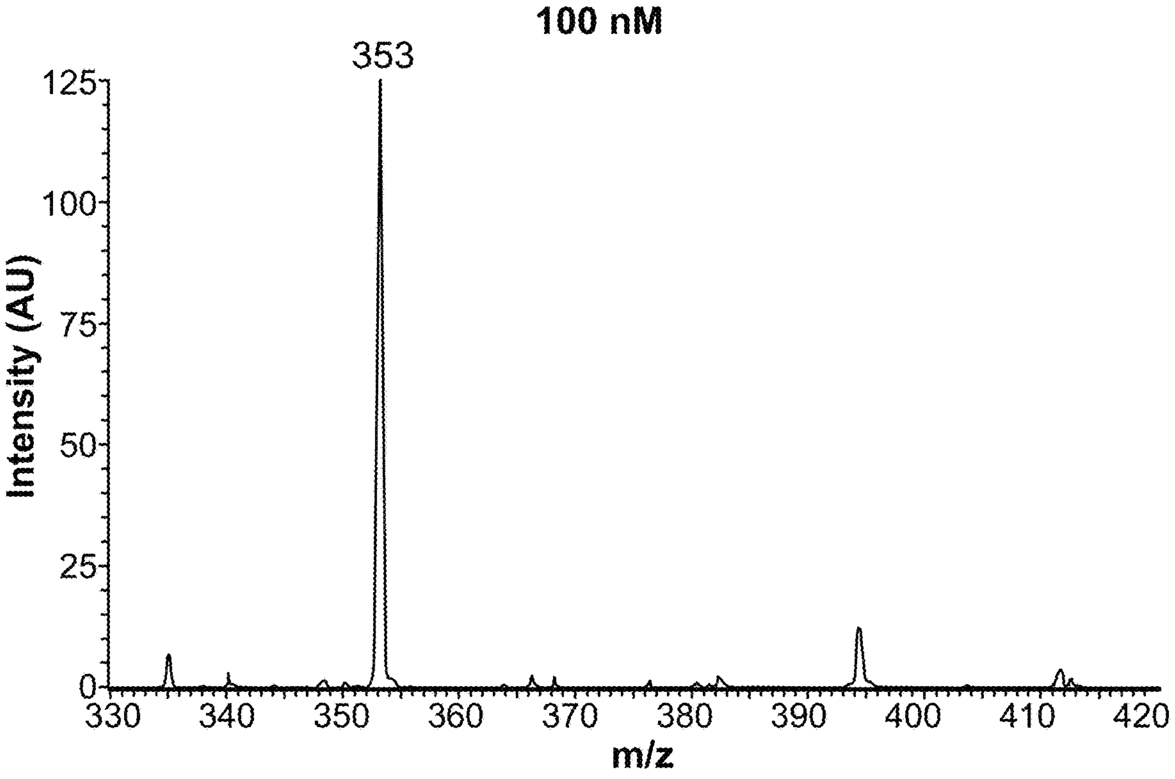
Figure 9A:
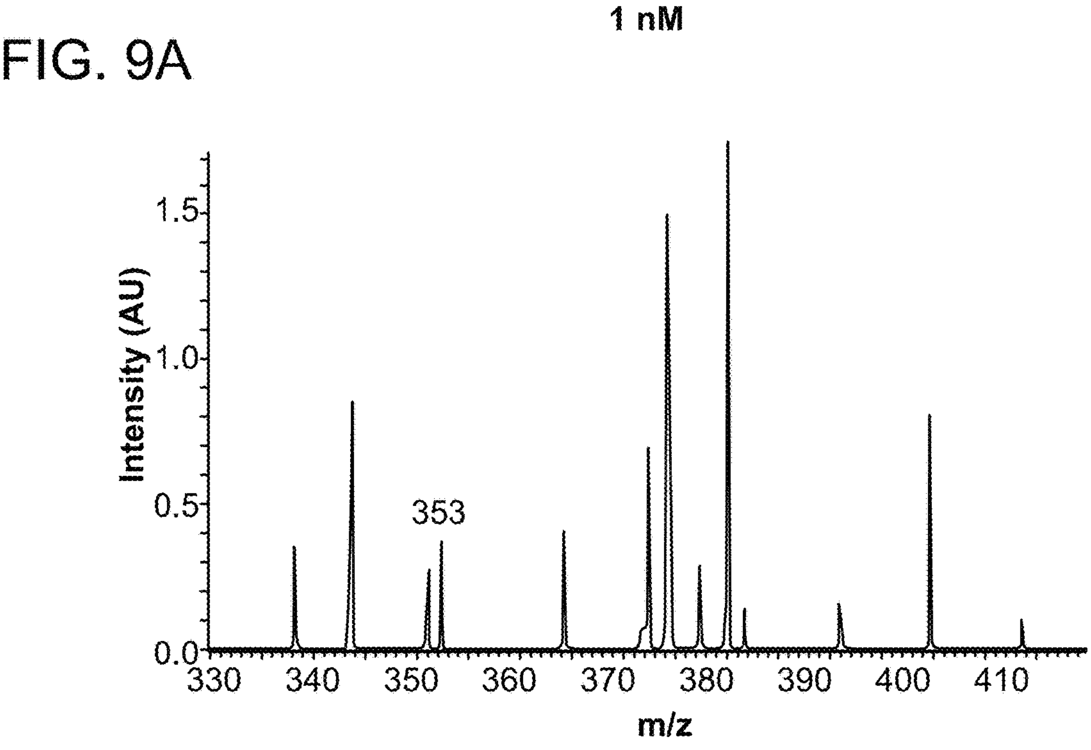
FIGS. 9A-C are a set of mass spectra showing FC-2 peptide sprayed directly from an apparatus of the invention. The set of mass spectra are MS/MS spectra for m/z 412 generated from the peptide FC-2 at various concentrations.
Figure 9B:
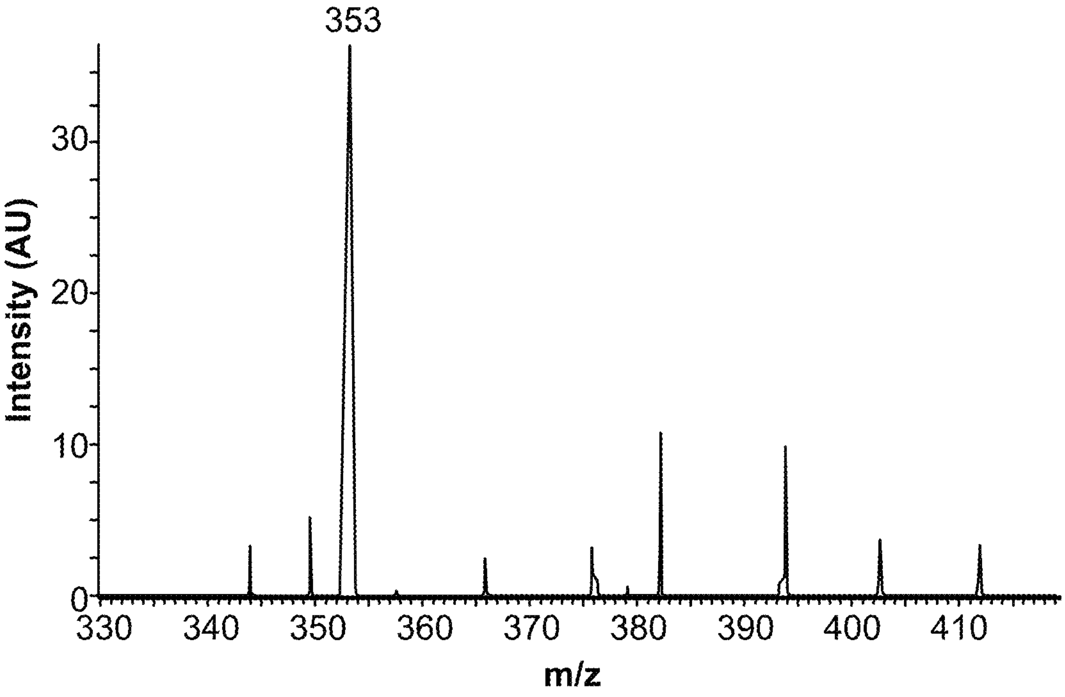
Figure 9C:
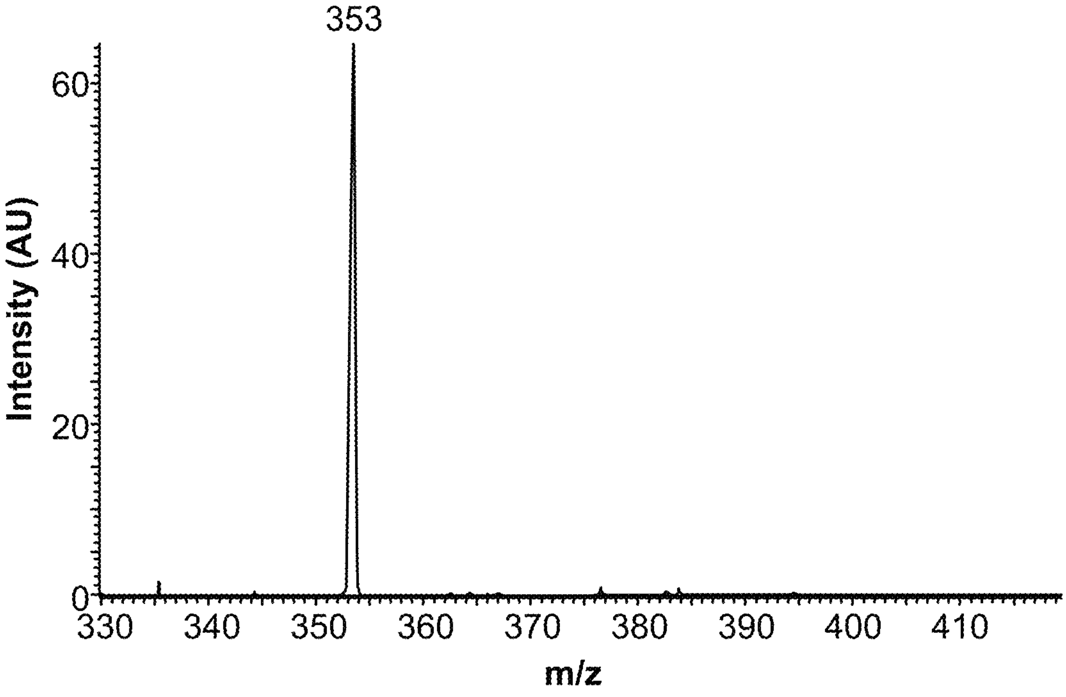

As mentioned above, an array of microwells and an electric field generator may be disposed to one another such that one or both may be moved in such a manner as to selectively activate an electric field for one or more of the microwells. An example, by way of illustration and not limitation, is shown in FIGS. 6-7. Apparatus 80 comprises array 70 and electric field generator 74. Robotic arm 72 controls the movement of array 70 and, optionally, robotic arm 76 controls the movement of electric field generator 74. Apparatus 80 also comprises a housing (not shown), which provides support for one or both of robotic arms 72 and 76. Each of robotic arm 72 and robotic arm 76 are separately controllable using suitable electronics and controllers (not shown) such that one or both of array 70 and electric field generator 74 may be moved with respect to one another. The mass spectrometer inlet is aligned with movement of the electric field generator. In that manner an electric field may be applied selectively to one or more of apparatus 80 comprising array 70 thereby allowing for interrogation of specific region(s) of the essentially non-absorbent membrane of the microwells of array 70. Ionization of droplets may be achieved from distinct regions of the essentially non-absorbent membrane by application of an electrical potential to that region only or by using external structures, including nanostructures, to facilitate ionization from selected regions. Furthermore, array 70 may be disposed with respect to the intake of a mass spectrometer so that droplets of liquid selectively released from the membranes may be subjected to mass spectral analysis (see FIG. 4).

It should be noted that in the example shown in FIGS. 6-7, the robotic arm controlling electric field generator 74 is shown above array 70. This is by way of illustration only; in some examples robotic arm 76 may be below array 70 or adjacent (on the side) of array 70, for example.

The apparatuses of the invention have application in any situation in which release of precise small volumes of liquid on a membrane is desired. Examples of such applications include, by way of illustration and not limitation, detection of target rare molecules, non-rare molecules, non-rare cells and rare cells, for example. In some examples, the essentially non-absorbent membrane comprises more than one pore and the electrical field is activated to selectively release droplets from an individual pore or subset of pores. The released droplets are subjected to mass spectrometry analysis to determine an area adjacent the individual pore or subset of pores where a particular MS label is located. The liquid on the membrane corresponding to the area is removed for analysis by methods discussed more fully below. The liquid adjacent the individual pore may be removed by suction, punching out the area of the membrane, lifting, dissection, or extraction, for example, or a combination of two or more thereof.

Inductive Charging

In inductive electrospray ionization, as described for example in U.S. Pat. No. 9,184,036, the content of which is incorporated by reference herein in its entirety, a potential may be applied to one or more electrodes (e.g., the electric field generator) placed close to the essentially non-absorbent membrane that contains the sample. It pulses repeatedly in either the positive or negative mode at a frequency ranging from 10-2000 Hz. Strong dynamic electromagnetic fields are produced in the essentially non-absorbent membrane, and give the focus of the field, in the specifically targeted pore of the essentially non-absorbent membrane, resulting in a burst of charged droplets from the pore.

In inductive charging, the high voltage source (e.g., the electric field generator) is not in contact with sample or the essentially non-absorbent membrane that contains the sample. In this manner, the ions are generated by inductive charging, i.e., an inductive method is used to charge the primary microdroplets. This allows for controlled and focused droplet creation. The generated droplets are directed into the mass spectrometer.

Charged droplet creation from a specific location on the essentially non-absorbent membrane can be achieved by placing an electrode (e.g., the electric field generator) near the desired pore of the essentially non-absorbent membrane (typically 2-5 mm distant) and pulsing it repetitively to high positive potentials (5-7 kV, 50-3,000 Hz, pulse width ~0.2-2 ms). Electromagnetic induction produces high electrical fields in proximity to the specific pore of the essentially non-absorbent membrane that result in bursts of charged droplets from only that pore of the essentially non-absorbent membrane.

In some examples, liquid containing an MS label as discussed herein can be directly discharged from an essentially non-absorbent membrane bearing mass tagged rare cells or particles after applying a mass tag release agent. Accordingly, ambient electrostatic focusing of emitted charged microdroplets/solvated ions to a smaller area such as the entrance to a mass spectrometer is achieved. In some examples, electrical field assisted charged droplet emission is achieved with nanofeatures provided by an array of points above or below the essentially non-absorbent membrane to provide a high electric field adjacent to a surface of the essentially non-absorbent membrane.

In some examples, intrinsic nanofeatures of the essentially non-absorbent membrane may be used to create a spray of analyte-bearing ions from the wetted essentially non-absorbent membrane by charged droplet field emission. A combination of pneumatic and electrostatic forces may be employed to collect ions for subsequent analysis by a mass spectrometer. This includes cases in which pneumatic forces are provided either by suction from a mass spectrometer inlet (such as by vacuum) or by gas flow provided independent of a mass spectrometer.

Desorption Electrospray Ionization

One embodiment for generating an ion beam to be directed at the sample on the essentially non-absorbent membrane employs Desorption electrospray ionization (DESI), which is described for example in Takats et al. (U.S. Pat. No. 7,335,897), the content of which is incorporated by reference herein in its entirety. DESI allows ionizing and desorbing a material (analyte) at atmospheric or reduced pressure under ambient conditions. A DESI system generally includes a device for generating a DESI-active spray by delivering droplets of a liquid into a nebulizing gas. The system also includes a means for directing the DESI-active spray onto a surface. It is understood that the DESI-active spray may, at the point of contact with the surface, include both or either charged and uncharged liquid droplets, gaseous ions, molecules of the nebulizing gas and of the atmosphere in the vicinity. The pneumatically assisted spray is directed onto the essentially non-absorbent membrane holding the sample where it interacts with one or more analytes, if present in the sample, and generates desorbed ions of the analyte or analytes that are ejected through the pore of the essentially non-absorbent membrane. The desorbed ions can be directed to a mass analyzer for mass analysis, to an IMS device for separation by size and measurement of resulting voltage variations, to a flame spectrometer for spectral analysis, or the like.

Figure 11:
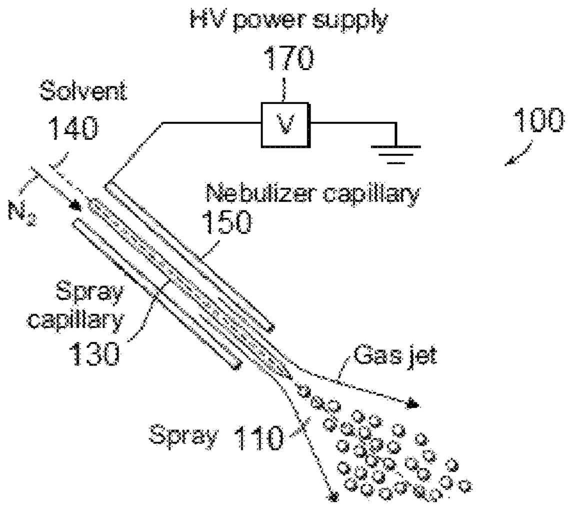
FIG. 11 shows a schematic showing a spray device for generating and directing a DESI-active spray.

FIG. 11 illustrates schematically one embodiment of a DESI system 100. In this system, a spray 110 is generated by a conventional electrospray device 120. The device 120 includes a spray capillary 130 through which the liquid solvent 140 is fed. A surrounding nebulizer capillary 150 forms an annular space through which a nebulizing gas such as nitrogen ($N_2$) is fed at high velocity. In one example, the liquid was a water/methanol mixture and the gas was nitrogen. A high voltage is applied to the liquid solvent by a power supply 170 via a metal connecting element. The result of the fast flowing nebulizing gas interacting with the liquid leaving the capillary 130 is to form the DESI-active spray 110 comprising liquid droplets. DESI-active spray 110 also may include neutral atmospheric molecules, nebulizing gas, and gaseous ions. Although an electrospray device 120 has been described, any device capable of generating a stream of liquid droplets carried by a nebulizing gas jet may be used to form the DESI-active spray 11.

The spray 110 is directed onto the essentially non-absorbent membrane holding the sample. The desorbed ions leaving the sample through the pore of the essentially non-absorbent membrane are collected and introduced into the atmospheric inlet or interface of a mass spectrometer for analysis. The essentially non-absorbent membrane may be a moveable platform or may be mounted on a moveable platform that can be moved in the x, y or z directions by well-known drive means to desorb and ionize the sample at different areas. Electric potential and temperature of the platform may also be controlled by known means. Any atmospheric interface that is normally found in mass spectrometers will be suitable for use in the invention. Good results have been obtained using a typical heated capillary atmospheric interface. Good results also have been obtained using an atmospheric interface that samples via an extended flexible ion transfer line made either of metal or an insulator.

Low Temperature Plasma

One embodiment for generating an ion beam to be directed at the sample on the essentially non-absorbent membrane employs a low temperature plasma (LTP) probe, which is described in Ouyang et al. (U.S. Pat. No. 8,519,354), the content of each of which is incorporated by reference herein in its entirety. Unlike electrospray or laser based ambient ionization sources, plasma sources do not require an electrospray solvent, auxiliary gases, and lasers. LTP can be characterized as a non-equilibrium plasma having high energy electrons, with relatively low kinetic energy but reactive ions and neutrals; the result is a low temperature ambient plasma that can be used to desorb and ionize analytes from surfaces and produce molecular ions or fragment ions of the analytes. A distinguishing characteristic of the LTP, in comparison with high temperature (equilibrium) plasmas, is that the LTP does not breakdown the molecules into atoms or small molecular fragments, so the molecular information is retained in the ions produced. LTP ionization sources have the potential to be small in size, consume low power and gas (or to use only ambient air) and these advantages can lead to reduced operating costs. In addition to cost savings, LTP based ionization methods have the potential to be utilized with portable mass spectrometers for real-time analytical analysis in the field (Gao, L.; Song, Q.; Patterson, G. E.; Cooks, D. Ouyang, Z., Anal. Chem. 2006, 78, 5994-6002; Mulligan, C. C.; Talaty, N.; Cooks, R. G., Chemical Communications 2006, 1709-1711; and Mulligan, C. C.; Justes, D. R.; Noll, R. J.; Sanders, N. L.; Laughlin, B. C.; Cooks, R. G., The Analyst 2006, 131, 556-567).

Figure 12:
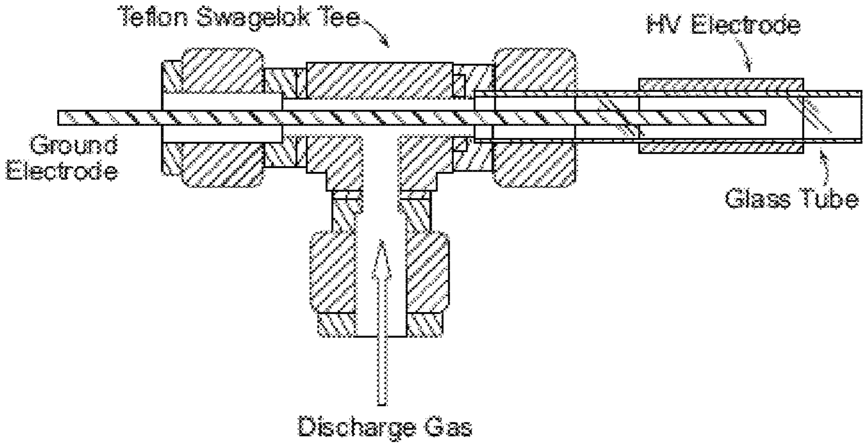
FIG. 12 shows a schematic showing an embodiment of a low temperature plasma (LTP) probe.

An exemplary LTP probe is shown in FIG. 12. Such a probe may include a housing having a discharge gas inlet port, a probe tip, two electrodes, and a dielectric barrier, in which the two electrodes are separated by the dielectric barrier, and in which application of voltage from a power supply generates an electric field and a low temperature plasma, in which the electric field, or gas flow, or both, propel the low temperature plasma out of the probe tip. The ionization source of the probe described herein is based upon a dielectric barrier discharge (DBD; Kogelschatz, U., Plasma Chemistry and Plasma Processing 2003, 23, 1-46). Dielectric barrier discharge is achieved by applying a high voltage signal, for example an alternating current, between two electrodes separated by a dielectric barrier. A non-thermal, low power, plasma is created between the two electrodes, with the dielectric limiting the displacement current. This plasma contains reactive ions, electrons, radicals, excited neutrals, and metastable species in the ambient environment of the sample which can be used to desorb/ ionize molecules from a solid sample surface as well as ionizing liquids and gases. The plasma can be extracted from the discharge region and directed toward the sample surface with the force by electric field, or the combined force of the electric field and gas flow.

In certain embodiments, the probe further includes a power supply. The power supply can provide direct current or alternating current. In certain embodiments, the power supply provides an alternating current. In certain embodiments, a discharge gas is supplied to the probe through the discharge gas inlet port, and the electric field and/or the discharge gas propel the low temperature plasma out of the probe tip. The discharge gas can be any gas. Exemplary discharge gases include helium, compressed or ambient air, nitrogen, and argon. In certain embodiments, the dielectric barrier is composed of an electrically insulating material. Exemplary electrically insulating materials include glass, quartz, ceramics and polymers. In other embodiments, the dielectric barrier is a glass tube that is open at each end. In other embodiments, varying the electric field adjusts the energy and fragmentation degree of ions generated from the analytes in a sample.

The plasma discharge from the low temperature plasma probe is directed onto the essentially non-absorbent membrane holding the sample. The plasma interacts with the sample and causes a liquid droplet of the sample to be ejected through the pore of the essentially non-absorbent membrane and introduced into the atmospheric inlet or interface of a mass spectrometer for analysis.

Ionization Using Wetted Porous Material

Figure 13:
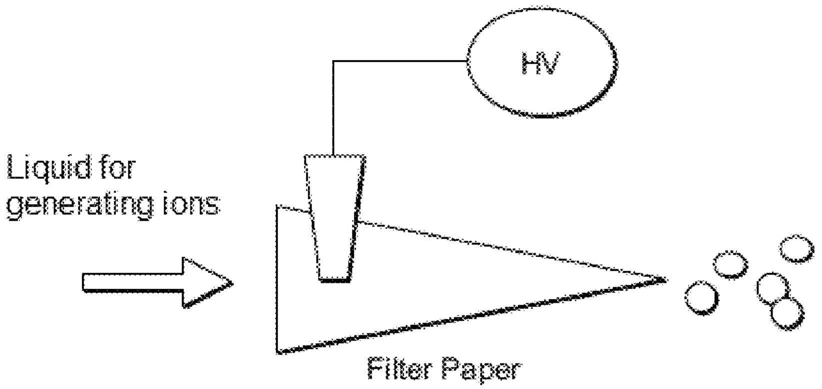
FIG. 13 shows a schematic of a liquid for generating ions being fed to a piece of paper for generation of an ion beam.

One embodiment for generating an ion beam to be directed at the sample on the essentially non-absorbent membrane employs a probe comprised of porous material that is wetted to produce ions, which is described in Ouyang et al. (U.S. Pat. No. 8,859,956), the content of each of which is incorporated by reference herein in its entirety. An exemplary probe is shown in FIG. 13. Porous materials, such as paper (e.g. filter paper or chromatographic paper) or other similar materials are used to hold and transfer liquids an ion beam generated directly from the edges of the material when a high electric voltage is applied to the material. The porous material is kept discrete (i.e., separate or disconnected) from a flow of solvent, such as a continuous flow of solvent. Instead, liquid is spotted onto the porous material. The spotted liquid is then connected to a high voltage source to produce an ion beam of the liquid that is directed onto the essentially non-absorbent membrane holding the sample. The desorbed ions leaving the sample through the pore of the essentially non-absorbent membrane are collected and introduced into the atmospheric inlet or interface of a mass spectrometer for analysis. The liquid is transported through the porous material without the need of a separate solvent flow. Pneumatic assistance is not required; rather, a voltage is simply applied to the porous material.

In certain embodiments, the porous material is any cellulose-based material. In other embodiments, the porous material is a non-metallic porous material, such as cotton, linen wool, synthetic textiles, or plant tissue. In still other embodiments, the porous material is paper. Advantages of paper include: cost (paper is inexpensive); it is fully commercialized and its physical and chemical properties can be adjusted; it can filter particulates (cells and dusts) from liquid samples; it is easily shaped (e.g., easy to cut, tear, or fold); liquids flow in it under capillary action (e.g., without external pumping and/or a power supply); and it is disposable.

In certain embodiments, the porous material is integrated with a solid tip having a macroscopic angle that is optimized for spray.

In particular embodiments, the porous material is filter paper. Exemplary filter papers include cellulose filter paper, ashless filter paper, nitrocellulose paper, glass microfiber filter paper, and polyethylene paper. Filter paper having any pore size may be used. Exemplary pore sizes include Grade 1 (11 μm), Grade 2 (8 μm), Grade 595 (4-7 μm), and Grade 6 (3 μm). Pore size will not only influence the transport of liquid inside the spray materials, but could also affect the formation of the Taylor cone at the tip. The optimum pore size will generate a stable Taylor cone and reduce liquid evaporation. The pore size of the filter paper is also an important parameter in filtration, i.e., the paper acts as an online pretreatment device. Commercially available ultra filtration membranes of regenerated cellulose, with pore sizes in the low nm range, are designed to retain particles as small as 1000 Da. Ultra filtration membranes can be commercially obtained with molecular weight cutoffs ranging from 1000 Da to 100,000 Da.

Probes of the invention work well for the generation of micron scale droplets simply based on using the high electric field generated at an edge of the porous material. In particular embodiments, the porous material is shaped to have a macroscopically sharp point, such as a point of a triangle, for ion generation. Probes of the invention may have different tip widths. In certain embodiments, the probe tip width is at least about 5 μm or wider, at least about 10 μm or wider, at least about 50 μm or wider, at least about 150 μm or wider, at least about 250 μm or wider, at least about 350 μm or wider, at least about 400μ or wider, at least about 450 μm or wider, etc. In particular embodiments, the tip width is at least 350 μm or wider. In other embodiments, the probe tip width is about 400 μm. In other embodiments, probes of the invention have a three dimensional shape, such as a conical shape.

Detection of Target Rare Molecules

In some examples, the apparatuses of the invention are used in the detection of different populations of target rare molecules employing affinity agents and different labels that are detectable using MS techniques. In some examples, one or more alteration agents are used to generate MS labels that are chosen to differentiate among different populations of target rare molecules. The methods also employ separation methods, in which liquid droplets are produced and are examined by MS techniques for one or both of the presence and amount of each different MS label. Differentiation of the MS labels yields information about one or both of the presence and amount of each different population of target rare molecules. The number of MS labels may be as many as $10^6$ or more per target rare molecule or as few as 10 per target rare molecule. The number of MS labels per target rare molecule may be about 10 to about $10^{12}$, or about 10 to about $10^{10}$, or about 10 to about $10^8$, or about 10 to about $10^6$, or about 10 to about $10^4$, or about 10 to about 100, or about 100 to about $10^{10}$, or about 100 to about $10^8$, or about 100 to about $10^6$, or about 100 to about $10^4$, for example.

In some examples, the methods are for detecting one or more different populations of target rare molecules in a sample suspected of containing the one or more different populations of rare molecules and non-rare molecules. The sample in liquid form is contacted to a microwell that comprises an essentially non-absorbent membrane. Optionally, the concentration of the one or more different populations of target rare molecules is enhanced over that of the non-rare molecules to form a concentrated sample by employing a suitable technique such as, for example, filtration. The sample is incubated with, for each different population of target rare molecules, an affinity agent that comprises a specific binding partner that is specific for and binds to a target rare molecule of one of the populations of the target rare molecules. The affinity agent comprises a mass spectrometry label precursor or a first alteration agent. The affinity agent may be non-particulate or particulate. The first alteration agent either facilitates the formation of a mass spectrometry label from the mass spectrometry label precursor or releases an entity that comprises the mass spectrometry label precursor from the affinity agent. If the first alteration agent does not facilitate the formation of a mass spectrometry label from the mass spectrometry label precursor, the sample is subjected to a second alteration agent that facilitates the formation of a mass spectrometry label from the mass spectrometry label precursor. The mass spectrometry label corresponds to or comprises one of the populations of target rare molecules. The sample on the essentially non-absorbent membrane is exposed to an electrical field to release droplets of the sample through the at least one pore of the essentially non-absorbent membrane. The droplets are subjected to mass spectrometry analysis to determine the presence and/or amount of each different mass spectrometry label. The presence and/or amount of each different mass spectrometry label to the present and/or amount of each different population of target rare molecules in the sample for each microwell.

In one approach, particle amplification is utilized and provides for aggregating or clustering particles to form particle aggregates. In one example, a larger particle (carrier particle) can be coated by many smaller particles (label particles). To further achieve amplification, the carrier particle can be chained with other carrier particles using one or more linking groups. The label particle contains the MS label on the surface, which may be on the order of $10^5$ since the size of mass label is comparatively small. In this approach, very low background levels are realized. The carrier particles and label particles should have a diameter that is smaller than the pores in the essentially non-absorbent membrane.

It should be noted that one or more of the identification techniques discussed below may be applied to a sample subsequent to contacting the sample with an essentially non-absorbent membrane in accordance with the principles described herein. Thus, approaches for analysis of samples to identify one or more target rare molecules include first identifying which microwells have target rare molecules of interest. Thus, techniques may be employed as a screening technique to identify microwells that have sample with target rare molecules for subsequent analysis.

The sample to be analyzed is one that is suspected of containing target rare molecules, non-rare cells and rare cells. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, and mucus, for example. Biological tissue includes, by way of illustration, hair, skin, sections or excised tissues from organs or other body parts, for example. In many instances, the sample is whole blood, plasma or serum. Rare cells may be from, for example, lung, bronchus, colon, rectum, pancreas, prostate, breast, liver, bile duct, bladder, ovary, brain, central nervous system, kidney, pelvis, uterine corpus, oral cavity or pharynx or melanoma cancers. The rare cells may be, but are not limited to, pathogens such as bacteria, virus, fungus, and protozoa; malignant cells such as malignant neoplasms or cancer cells; circulating endothelial cells; circulating tumor cells; circulating cancer stem cells; circulating cancer mesochymal cells; circulating epithelial cells; fetal cells; immune cells (B cells, T cells, macrophages, NK cells, monocytes); and stem cells; for example. In some examples, the sample to be tested is a blood sample from a mammal such as, but not limited to, a human subject. The blood sample is one that contains cells such as, for example, non-rare cells and rare cells. In some examples the blood sample is whole blood or plasma.

The phrase "target rare molecule" refers to a molecule including biomarkers that may be detected in a sample where the molecule or biomarker is indicative of a particular population of cells. Target rare molecules include, but are not limited to, antigens (such as, for example, proteins, peptides, hormones, vitamins, allergens, autoimmune antigens, carbohydrates, lipids, glycoproteins, co-factors, antibodies, and enzymes) and nucleic acids.

The phrase "population of target rare molecules" refers to a group of molecules that share a common antigen or nucleic acid that is specific for the group of molecules. The phrase "specific for" means that the common antigen or nucleic acid distinguishes the group of molecules from other molecules.

Non-rare molecules are present in relatively large amounts when compared to an amount of rare molecules in a sample.

The phrase "population of cells" refers to a group of cells having an antigen or nucleic acid on their surface or inside the cell in which the antigen is common to all of the cells of the group and where the antigen is specific for the group of cells.

Rare cells are those cells that are present in a sample in relatively small quantities when compared to the amount of non-rare cells in a sample. In some examples, the rare cells are present in an amount of about $10^{-8}$% to about $10^{-2}$% by weight of a total cell population in a sample suspected of containing the rare cells. The rare cells may be, but are not limited to, malignant cells such as malignant neoplasms or cancer cells; circulating endothelial cells; circulating epithelial cells; mesochymal cells; fetal cells; immune cells (B cells, T cells, macrophages, NK cells, monocytes); stem cells; nucleated red blood cells (normoblasts or erythroblasts); and immature granulocytes.

Non-rare cells are those cells that are present in relatively large amounts when compared to the amount of rare cells in a sample. In some examples, the non-rare cells are at least about 10 times, or at least about $10^2$ times, or at least about $10^3$ times, or at least about $10^4$ times, or at least about $10^5$ times, or at least about $10^6$ times, or at least about $10^7$ times, or at least about $10^8$ times greater than the amount of the rare cells in the total cell population in a sample suspected of containing non-rare cells and rare cells. The non-rare cells may be, but are not limited to, white blood cells, platelets, and red blood cells, for example.

Target rare molecules of rare cells include, but are not limited to, cancer cell type biomarkers, oncoproteins and oncogenes, chemo resistance biomarkers, metastatic potential biomarkers, and cell typing markers, for example. Cancer cell type biomarkers include, by way of illustration and not limitation, cytokeratins (CK) (CK1, CK2, CK3, CK4, CK5, CK6, CK7, CK8 and CK9, CK10, CK12, CK 13, CK14, CK16, CK17, CK18, CK19 and CK2), epithelial cell adhesion molecule (EpCAM), N-cadherin, E-cadherin and vimentin, for example. Oncoproteins and oncogenes with likely therapeutic relevance due to mutations include, but are not limited to, WAF, BAX-1, PDGF, JAGGED 1, NOTCH, VEGF, VEGHR, CA1X, MIB1, MDM, PR, ER, SELS, SEMI, PI3K, AKT2, TWIST1, EML-4, DRAFF, C-MET, ABL1, EGFR, GNAS, MLH1, RET, MEK1, AKT1, ERBB2, HER2, HNF1A, MPL, SMAD4, ALK, ERBB4, HRAS, NOTCH1, SMARCB1, APC, FBXW7, IDH1, NPM1, SMO, ATM, FGFR1, JAK2, NRAS, SRC, BRAF, FGFR2, JAK3, RA, STK11, CDH1, FGFR3, KDR, PIK3CA, TP53, CDKN2A, FLT3, KIT, PTEN, VHL, CSF1R, GNA11, KRAS, PTPN11, DDR2, CTNNB1, GNAQ, MET, RB1, AKT1, BRAF, DDR2, MEK1, NRAS, FGFR1, and ROS1, for example.

Endothelial cell typing markers include, by way of illustration and not limitation, CD136, CD105/Endoglin, CD144/VE-cadherin, CD145, CD34, Cd41 CD136, CD34, CD90, CD31/PECAM-1, ESAM,VEGFR2/Fik-1, Tie-2, CD202b/TEK, CD56/NCAM, CD73/VAP-2, claudin 5, Z0-1, and vimentin, for example.

Metastatic potential biomarkers include, but are limited to, urokinase plasminogen activator (uPA), plasminogen activator inhibitor (PAI-1), CD95, serine proteases (e.g., plasmin and ADAM, for example); serine protease inhibitors (e.g., Bikunin); matrix metalloproteinases (e.g., MMP9); matrix metalloproteinase inhibitors (e.g., TIMP-1). Chemoresistance biomarkers include, by way of illustration and not limitation, PL2L piwi like, 5T4, ADLH, β-integrin, a6 integrin, c-kit, c-met, LIF-R, CXCR4, ESA, CD 20, CD44, CD133, CKS, TRAF2 and ABC transporters, cancer cells that lack CD45 or CD31 but contain CD34 are indicative of a cancer stem cell; and cancer cells that contain CD44 but lack CD24.

In methods herein, white blood cells may be excluded as non-rare cells. For example, markers such as, but not limited to, CD45, CTLA-4, CD4, CD6S and CDS that are present on white blood cells can be used to indicate that a cell is not a rare cell of interest. In a particular non-limiting example, CD45 antigen (also known as protein tyrosine phosphatase receptor type C or PTPRC) and originally called leukocyte common antigen is useful in detecting all white blood cells.

Additionally, CD45 can be used to differentiate different types of white blood cells that might be considered rare cells. For example, granulocytes are indicated by CD45+, CD15+; monocytes are indicated by CD45+, CD14+; T lymphocytes are indicated by CD45+, CD3+; T helper cells are indicated by CD45+, CD3+, CD4+; cytotoxic T cells are indicated by CD45+, CD3+, CDS+; β-lymphocytes are indicated by CD45+, CD19+ or CD45+, CD20+; thrombocytes are indicated by CD45+, CD61+; and natural killer cells are indicated by CD16+, CD56+, and CD3-. Furthermore, two commonly used CD molecules, namely, CD4 and CD8, are, in general, used as markers for helper and cytotoxic T cells, respectively. These molecules are defined in combination with CD3+, as some other leukocytes also express these CD molecules (some macrophages express low levels of CD4; dendritic cells express high levels of CDS).

In other cases the rare cell is a pathogen, which includes, but is not limited to, gram-positive bacteria (e.g., *Enterococcus* sp. Group B *Streptococcus*, Coagulase-negative *staphylococcus* sp. *Streptococcus viridans, Staphylococcus aureus* and *saprophyticus, Lactobacillus* and resistant strains thereof, for example); yeasts including, but not limited to, *Candida albicans*, for example; gram-negative bacteria such as, but not limited to, *Escherichia coli, Klebsiella pneumoniae, Citrobacter koseri, Citrobacter freundii, Klebsiella oxytoca, Morganella morganii, Pseudomonas aeruginosa, Proteus mirabilis, Serratia marcescens*, and Diphtheroids (gnb) and resistant strains thereof, for example; viruses such as, but not limited to, HIV, HPV, Flu, and MERSA, for example; and sexually transmitted diseases. In the case of detecting rare cell pathogens, a particle reagent is added that comprises a binding partner, which binds to the rare cell pathogen population. Additionally, for each population of cellular target rare molecules on the pathogen, a reagent is added that comprises a binding partner for the cellular target rare molecule, which binds to the cellular target rare molecules in the population.

The phrase "non-cellular target rare molecules" refers to target rare molecules that are not bound to a cell and/or that freely circulate in a sample. Such non-cellular target rare molecules include biomolecules useful in medical diagnosis of diseases, which include, but are not limited to, biomarkers for detection of cancer, cardiac damage, cardiovascular disease, neurological disease, hemostasis/hemastasis, fetal maternal assessment, fertility, bone status, hormone levels, vitamins, allergies, autoimmune diseases, hypertension, kidney disease, diabetes, liver diseases, infectious diseases and other biomolecules useful in medical diagnosis of diseases, for example.

As mentioned above, in some instances, one or more of the populations of target rare molecules may be a population of non-cellular target rare molecules. In such an instance, for each population of non-cellular target rare molecules, a capture particle entity is added that comprises a binding partner for the non-cellular target rare molecule, which binds to the non-cellular target rare molecules in the population to form particle-bound non-cellular target rare molecules thereby rendering a non-cellular target rare molecule in particulate form for purposes of carrying out an enhancement of a concentration of one or different populations of a non-cellular target rare molecule over that of non-rare molecules to form a concentrated sample.

The composition of the particle may be organic or inorganic, magnetic or non-magnetic. Organic polymers include, by way of illustration and not limitation, nitrocellulose, cellulose acetate, poly(vinyl chloride), polyacrylamide, polyacrylate, polyethylene, polypropylene, poly(4-methylbutene), polystyrene, poly(methyl methacrylate), poly(hydroxyethyl methacrylate), poly(styrene/divinylbenzene), poly(styrene/acrylate), poly(ethylene terephthalate), melamine resin, nylon, poly(vinyl butyrate), for example, either used by themselves or in conjunction with other materials and including latex, microparticle and nanoparticle forms thereof. The particles may also comprise carbon (e.g., carbon nanotubes), metal (e.g., gold, silver, and iron, including metal oxides thereof), colloids, dendrimers, dendrons, nucleic acids, Branch chain-DNA, and liposomes, for example.

The diameter of the particles of the particle entity is dependent on one or more of the nature of the target rare molecule, the nature of the sample, the nature and the pore size of the essentially non-absorbent membrane, the adhesion of the particle to the membrane, the surface of the particle, the surface of the essentially non-absorbent membrane, the liquid ionic strength, liquid surface tension and components in the liquid, and the number, size, shape and molecular structure of attached affinity agent and MS label precursors, for example. The diameter of the particles must be large enough to reduce background contribution to an acceptable level but not so large as to achieve inefficient separation of the particles from non-rare molecules. In some examples in accordance with the principles described herein, the average diameter of the particles should be at least about 0.02 microns (20 nm) and not more than about 200 microns, or not more than about 120 microns. In some examples, the particles have an average diameter from about 0.1 microns to about 20 microns, or about 0.1 microns to about 15 microns, or about 0.1 microns to about 10 microns, or about 0.02 microns to about 0.2 microns, or about 0.2 microns to about 1 micron, or about 1 micron to about 5 microns, or about 1 micron to about 20 microns, or about 1 micron to about 15 microns, or about 1 micron to about 10 microns, or about 5 microns to about 20 microns, or about 5 to about 15 microns, or about 5 to about 10 microns, or about 6 to about 15 microns, or about 6 to about 10 microns, for example. In some examples, the adhesion of the particles to the surface is so strong that the particle diameter can be smaller than the pore size of the essentially non-absorbent membrane. In other examples, the particles are sufficiently larger than the pore size of the essentially non-absorbent membrane such that physically the particles cannot fall through the pores of the essentially non-absorbent membrane.

The capture particle entity also includes a binding partner that is specific for the non-cellular target rare molecule. The phrase "binding partner" refers to a molecule that is a member of a specific binding pair. A member of a specific binding pair is one of two different molecules having an area on the surface or in a cavity, which specifically binds to and is thereby defined as complementary with a particular spatial and polar organization of the other molecule. The members of the specific binding pair may be members of an immunological pair such as antigen-antibody or hapten-antibody, biotin-avidin, hormones-hormone receptors, enzyme-substrate, nucleic acid duplexes, IgG-protein A, and polynucleotide pairs such as DNA-DNA or DNA-RNA. The binding partner may be bound, either covalently or non-covalently, to the particle of the particle reagent. "Non-covalently" means that the binding partner is bound to the particle as the result of one or more of hydrogen bonding, van der Waals forces, electrostatic forces, hydrophobic effects, physical entrapment in the particles, and charged interactions. "Covalently" means that the binding partner is bound to the particle by a bond or a linking group, which may be aliphatic or aromatic and may comprise a chain of 2 to about 60 or more atoms that include carbon, oxygen, sulfur, nitrogen and phosphorus.

In some examples, samples are collected from a body of a subject into a suitable container such as, but not limited to, a cup, a bag, a bottle, capillary, or a needle, for example. Blood samples may be collected into a VACUTAINER (blood collection tube, commercially available from BD). The container may contain a collection medium into which the sample is delivered. The collection medium is usually a dry medium and may comprise an amount of platelet deactivation agent effective to achieve deactivation of platelets in the blood sample when mixed with the blood sample.

Platelet deactivation agents include, but are not limited to, chelating agents such as, agents that comprise a triacetic acid moiety or a salt thereof, a tetraacetic acid moiety or a salt thereof, a pentaacetic acid moiety or a salt thereof, or a hexaacetic acid moiety or a salt thereof. In some examples, the chelating agent is ethylene diamine tetraacetic acid (EDTA) and its salts or ethylene glycol tetraacetate (EGTA) and its salts. The effective amount of platelet deactivation agent is dependent on one or more of the nature of the platelet deactivation agent, the nature of the blood sample, level of platelet activation and ionic strength, for example. In some examples, for EDTA as the anti-platelet agent, the amount of dry EDTA in the container is that which will produce a concentration of about 1.0 to about 2.0 mg/mL of blood, or about 1.5 mg/mL of the blood. The amount of the platelet deactivation agent is that which is sufficient to achieve at least about 90%, or at least about 95%, or at least about 99% of platelet deactivation.

As mentioned above, optionally, the concentration of the one or more different populations of target rare molecules is enhanced over that of the non-rare molecules to form a concentrated sample. In some examples, prior to contacting the sample with an essentially non-absorbent membrane, the sample is subjected to a filtration procedure using a porous matrix that retains the target rare molecules while allowing the non-rare molecules to pass through the porous matrix thereby enhancing the concentration of the target rare molecules. In the event that one or more target rare molecules are non-cellular, i.e., not associated with a cell or other biological particle, the sample is combined with one or more capture particle entities wherein each capture particle entity comprises a binding partner for the non-cellular target rare molecule of each of the populations of non-cellular target rare molecules to render the non-cellular target rare molecules in particulate form, i.e., to form particle-bound non-cellular target rare molecules. The combination of the sample and the capture particle entities is held for a period of time and at a temperature to permit the binding of non-cellular target rare molecules with corresponding binding partners of the capture particle entities. Moderate temperatures are normally employed, which may range from about 5° C. to about 70° C. or from about 15° C. to about 70° C. or from about 20° C. to about 45° C. The time period for an incubation period is about 0.2 seconds to about 6 hours, or about 2 seconds to about 1 hour, or about 1 to about 5 minutes, for example.

The time period for contact of the sample to the essentially non-absorbent membrane may be dependent for example on one or more of the nature and size of the different populations of target rare cells and/or particle-bound target rare molecules, the nature of the essentially non-absorbent membrane, the size of the pores of the essentially non-absorbent membrane, the level of vacuum applied to the sample on the essentially non-absorbent membrane, the volume to be filtered, and the surface area of the essentially non-absorbent membrane. In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes.

In methods herein, the sample, either unconcentrated or concentrated, may be incubated with, for each different population of target rare molecules, an affinity agent that comprises a binding partner that is specific for and binds to a target rare molecule of one of the populations of the target rare molecules. The affinity agent also comprises an MS label precursor or a first alteration agent that facilitates the formation of an MS label from each different MS label precursor or that releases an entity that comprises the MS label precursor from the affinity agent. In many examples, the above combination is provided in an aqueous medium, which may be solely water or which may also contain organic solvents such as, for example, polar aprotic solvents, polar protic solvents such as, e.g., dimethylsulfoxide (DMSO), dimethylformamide (DMF), acetonitrile, an organic acid, or an alcohol, and non-polar solvents miscible with water such as, e.g., dioxene, in an amount of about 0.1% to about 50%, or about 1% to about 50%, or about 5% to about 50%, or about 1% to about 40%, or about 1% to about 30%, or about 1% to about 20%, or about 1% to about 10%, or about 5% to about 40%, or about 5% to about 30%, or about 5% to about 20%, or about 5% to about 10%, by volume. In some examples, the pH for the aqueous medium is usually a moderate pH. In some examples, the pH of the aqueous medium is about 5 to about 8, or about 6 to about 8, or about 7 to about 8, or about 5 to about 7, or about 6 to about 7, or physiological pH. Various buffers may be used to achieve the desired pH and maintain the pH during any incubation period. Illustrative buffers include, but are not limited to, borate, phosphate (e.g., phosphate buffered saline), carbonate, TRIS, barbital, PIPES, HEPES, MES, ACES, MOPS, and BICINE.

An amount of aqueous medium employed is dependent on a number of factors such as, but not limited to, the nature and amount of the sample, the nature and amount of the reagents, the stability of target rare cells, and the stability of target rare molecules. In some examples, the amount of aqueous medium per 10 mL of sample is about 5 mL to about 100 mL, or about 5 mL to about 80 mL, or about 5 mL to about 60 mL, or about 5 mL to about 50 mL, or about 5 mL to about 30 mL, or about 5 mL to about 20 mL, or about 5 mL to about 10 mL, or about 10 mL to about 100 mL, or about 10 mL to about 80 mL, or about 10 mL to about 60 mL, or about 10 mL to about 50 mL, or about 10 mL to about 30 mL, or about 10 mL to about 20 mL, or about 20 mL to about 100 mL, or about 20 mL to about 80 mL, or about 20 mL to about 60 mL, or about 20 mL to about 50 mL, or about 20 mL to about 30 mL.

Where one or more of the target rare molecules are part of a cell, the aqueous medium may also comprise a lysing agent for lysing of cells. A lysing agent is a compound or mixture of compounds that disrupt the integrity of the membranes of cells thereby releasing intracellular contents of the cells. Examples of lysing agents include, but are not limited to, non-ionic detergents, anionic detergents, amphoteric detergents, low ionic strength aqueous solutions (hypotonic solutions), bacterial agents, aliphatic aldehydes, and antibodies that cause complement dependent lysis, for example. Various ancillary materials may be present in the dilution medium. All of the materials in the aqueous medium are present in a concentration or amount sufficient to achieve the desired effect or function.

In some examples, where one or more of the target rare molecules are part of a cell, it may be desirable to fix the cells of the sample. Fixation of the cells immobilizes the cells and preserves cell structure and maintains the cells in a condition that closely resembles the cells in an in vivo-like condition and one in which the antigens of interest are able to be recognized by a specific affinity agent. The amount of fixative employed is that which preserves the cells but does not lead to erroneous results in a subsequent assay. The amount of fixative may depend for example on one or more of the nature of the fixative and the nature of the cells. In some examples, the amount of fixative is about 0.05% to about 0.15% or about 0.05% to about 0.10%, or about 0.10% to about 0.15% by weight. Agents for carrying out fixation of the cells include, but are not limited to, cross-linking agents such as, for example, an aldehyde reagent (such as, e.g., formaldehyde, glutaraldehyde, and paraformaldehyde,); an alcohol (such as, e.g., C1-C5 alcohols such as methanol, ethanol and isopropanol); a ketone (such as a C3-C5 ketone such as acetone); for example. The designations C1-C5 or C3-C5 refer to the number of carbon atoms in the alcohol or ketone. One or more washing steps may be carried out on the fixed cells using a buffered aqueous medium.

If necessary after fixation, the cell preparation may also be subjected to permeabilization. In some instances, a fixation agent such as, an alcohol (e.g., methanol or ethanol) or a ketone (e.g., acetone), also results in permeabilization and no additional permeabilization step is necessary. Permeabilization provides access through the cell membrane to target molecules of interest. The amount of permeabilization agent employed is that which disrupts the cell membrane and permits access to the target molecules. The amount of permeabilization agent depends on one or more of the nature of the permeabilization agent and the nature and amount of the cells. In some examples, the amount of permeabilization agent is about 0.01% to about 10%, or about 0.1% to about 10%. Agents for carrying out permeabilization of the cells include, but are not limited to, an alcohol (such as, e.g., C1-C5 alcohols such as methanol and ethanol); a ketone (such as a C3-C5 ketone such as acetone); a detergent (such as, e.g., saponin, TRITON X-100 (4-(1,1,3,3-Tetramethylbutyl)phenyl-polyethylene glycol, t-Octylphenoxypolyethoxyethanol, Polyethylene glycol tert-octylphenyl ether buffer, commercially available from Sigma Aldrich), and TWEEN-20 (Polysorbate 20, commercially available from Sigma Aldrich)). One or more washing steps may be carried out on the permeabilized cells using a buffered aqueous medium.

As mentioned above, an affinity agent employed in methods herein is one that is specific for a target rare molecule. The affinity agent is a member of a specific binding pair, which is one of two different molecules, having an area on the surface or in a cavity, which specifically binds to and is thereby defined as complementary with a particular spatial and polar organization of the other molecule. The members of the specific binding pair may be members of an immunological pair such as antigen-antibody and hapten-antibody, although other specific binding pairs include, for example, biotin-avidin, hormones-hormone receptors, enzyme-substrate, aptamers, nucleic acid duplexes, IgG-protein A, and nucleic acid pairs such as DNA-DNA, DNA-RNA. In the case of cells, the affinity agent is an agent that specifically recognizes or binds to a target molecule antigen associated with a cell.

Specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules.

Antibodies specific for a target molecule for use in immunoassays to identify cells can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and $F(ab')_2$, and Fab', for example. In addition, aggregates, polymers, and conjugates of immunoglobulins or their fragments can be used where appropriate so long as binding affinity for a particular molecule is maintained.

Polyclonal antibodies and monoclonal antibodies may be prepared by techniques that are well known in the art. For example, in one approach monoclonal antibodies are obtained by somatic cell hybridization techniques. Monoclonal antibodies may be produced according to the standard techniques of Köhler and Milstein, *Nature* 265:495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981). In general, monoclonal antibodies can be purified by known techniques such as, but not limited to, chromatography, e.g., DEAE chromatography, ABx chromatography, and HPLC chromatography; and filtration, for example.

The affinity agent may be a nucleic acid (e.g., polynucleotide) that is complementary to a target nucleic acid. Polynucleotides refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides such as, for example, methylated nucleotides and nucleotide analogs. If present, modifications to the nucleotide structure may be imparted before or after assembly of the polymer. The sequence of nucleotides may be interrupted by non-nucleotide components. A polynucleotide may be further modified, such as by conjugation with a labeling component.

The affinity agent comprises either an MS label precursor or an alteration agent that facilitates the formation of an MS label from an MS label precursor where the MS label corresponds to a target rare molecule of one of the populations of target rare molecules. The MS label allows differentiation of one of the populations of target rare molecules from other populations of rare molecules. Furthermore, selection of the MS label may be carried out to avoid overlapping masses in the analysis by MS, to avoid background interference in the MS analysis, and to permit multiplexing.

The phrase "mass spectrometry label" or "MS label" refers to one or a group of molecules having unique masses, preferably below 3 kDA, such that each unique mass, corresponds to, and is used to determine a presence and/or amount of, each different population of target rare molecules. The MS labels are molecules of defined mass and include, but are not limited to, polypeptides, polymers, fatty acids, carbohydrates, organic amines, nucleic acids, and organic alcohols, for example, whose mass can be varied by substitution and chain size, for example. In the case of polymeric materials, the number repeating units is adjusted such that the mass is in a region that does not overlap with a background mass from the sample. The phrase "MS label" also includes an analyte that is captured by an affinity particle, a derivatized analyte where the derivatization renders the analyte ionic, and an underivatized analyte in ionic form. The MS label generates a unique mass pattern due to structure and fragmentation upon ionization.

The term "analyte" refers to a molecule or molecules that are to detected. Exemplary analytes by way of illustration and not limitation, include drugs, metabolites, pesticides and pollutants. Representative analytes, by way of illustration and not limitation, also include alkaloids, steroids, lactams, aminoalkylbenzenes, benzheterocyclics, purines, drugs derived from marijuana, hormones, polypeptides which includes proteins, immunosuppressants, vitamins, prostaglandins, tricyclic antidepressants, anti-neoplastics, nucleosides and nucleotides including polynucleosides and polynucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, and metabolites and derivatives of all of the above. Also included are metabolites related to disease states, aminoglycosides, such as gentamicin, kanamicin, tobramycin, and amikacin, and pesticides such as, for example, polyhalogenated biphenyls, phosphate esters, thiophosphates, carbamates and polyhalogenated sulfenamides and their metabolites and derivatives. The term "analyte" also includes combinations of two or more of polypeptides and proteins, polysaccharides and nucleic acids. Such combinations include, for example, components of bacteria, viruses, chromosomes, genes, mitochondria, nuclei and cell membranes. Protein analytes include, for example, immunoglobulins, cytokines, enzymes, hormones, cancer antigens, nutritional markers and tissue specific antigens. Such proteins include, by way of illustration and not limitation, protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in human plasma, blood clotting factors, protein hormones such as, e.g., follicle-stimulating hormone, luteinizing hormone, luteotropin, prolactin, chorionic gonadotropin, tissue hormones, cytokines, cancer antigens such as, e.g., PSA, CEA, $\alpha$-fetoprotein, acid phosphatase, CA19.9, CA15.3 and CA125, tissue specific antigens, such as, e.g., alkaline phosphatase, myoglobin, CPK-MB and calcitonin, and peptide hormones. Other polymeric materials of interest are mucopolysaccharides and polysaccharides. As indicated above, the term analyte further includes oligonucleotide and polynucleotide analytes such as mRNA, r-RNA, t-RNA, DNA and DNA-RNA duplexes, for example.

The "MS label precursor" is any molecule that results in an MS label by the action of the alteration agent. The MS label precursor may itself be an MS label that, through the action of the alteration agent is converted to another MS label by cleavage, by reaction with a moiety, by derivatization, or by addition or by subtraction of molecules, charges or atoms, for example, or a combination of two or more of the above.

The term "alteration agent" refers to a substance that has the ability to alter the MS label precursor. In certain embodiments, alteration agent is able to interact with the MS label precursor to achieve an MS label having a unique mass in the range of about 1 Da to about 3 kDa, or in the range of about 1 Da to about 50 Da, or in the range of about 50 Da, to about 150 Da, or in the range of about 150 Da to about 700 Da, or in the range of about 700 Da to about 3 kDa. In some examples the unique mass of the MS label is below about 3 kDa. The MS label precursor can be altered by bond breaking to form a neutral, negative or positive ion, or radical. The alteration of the MS label precursor by the alteration agent may be by addition of atoms, charges or electrons to, or subtraction of atoms, charges or electrons from, the MS label precursor or by bond cleavage in, or bond formation in, the MS label precursor. The alteration agents include, but are not limited to, chemical agents such as, but not limited to, catalysts (e.g., enzymes (including pseudoenzymes) and metals), oxidizing agents, reducing agents, acids, bases, agents that promote substitution reactions or replacement reactions; and ionization agents. In some examples, the alteration agent facilitates the formation of an MS label from the MS label precursor by promoting the reaction of the MS label precursor with a moiety to form the MS label, for example. In some examples the alteration agent facilitates the formation of an MS label from the MS label precursor by promoting the release of the MS label from the MS label precursor, for example.

The nature of the MS label precursors may be dependent for example on one or more of the nature of the MS label, the nature of the MS method employed, the nature of the MS detector employed, the nature of the target rare molecules, the nature of the affinity agent, the nature of any immunoassay employed, the nature of the sample, the nature of any buffer employed, the nature of the separation. In some examples, the MS label precursors are molecules whose mass can be varied by substitution and/or chain size. The MS labels produced from the MS label precursors are molecules of defined mass, which should not be present in the sample to be analyzed. Furthermore, the MS labels should be in the range detected by the MS detector, should not have overlapping masses and should be detectable by primary mass. Examples, by way of illustration and not limitation, of MS label precursors for use in methods of the invention include, by way of illustration and not limitation, polypeptides, organic and inorganic polymers, fatty acids, carbohydrates, cyclic hydrocarbons, aliphatic hydrocarbons, aromatic hydrocarbons, organic carboxylic acids, organic amines, nucleic acids, organic alcohols (e.g., alkyl alcohols, acyl alcohols, phenols, polyols (e.g., glycols), thiols, epoxides, primary, secondary and tertiary amines, indoles, tertiary and quaternary ammonium compounds, amino alcohols, amino thiols, phenolic amines, indole carboxylic acids, phenolic acids, vinylogous acid, carboxylic acid esters, phosphate esters, carboxylic acid amides, carboxylic acids from polyamides and polyesters, hydrazone, oxime, trimethylsilyl enol ether, acetal, ketal, carbamates, ureas, guanidines, isocyanates, sulfonic acids, sulfonamides, sulfonylureas, sulfates esters, monoglycerides, glycerol ethers, sphingosine bases, ceramines, cerebrosides, steroids, prostaglandins, carbohydrates, nucleosides and therapeutic drugs.

An MS label precursor can include 1 to about 100,000 MS labels, or about 10 to about 100,000 MS labels, or about 100 to about 100,000 MS labels, or about 1,000 to about 100,000 MS labels, or about 10,000 to about 100,000 MS labels. The MS label precursor can be comprised of proteins, polypeptides, polymers, particles, carbohydrates, nucleic acids, lipids or other macromolecules capable of including multiple repeating units of MS labels by attachment. Multiple MS labels allow amplification as every MS label precursor can generate many MS labels.

With polypeptide MS label precursors, for example, the chain length of the polypeptide can be adjusted to yield an MS label in a mass region without background peaks. Furthermore, MS labels may be produced from the MS label precursors having unique masses, which are not present in the sample tested. The polypeptide MS label precursors can comprise additional amino acids or derivatized amino acids, which allows methods to be multiplexed to obtain more than one result at a time. Examples of polypeptide MS label precursors include, but are not limited to, polyglycine, polyalanine, polyserine, polythreonine, polycysteine, polyvaline, polyleucine, polyisoleucine, polymethionine, polyproline, polyphenylalanine, polytyrosine, polytryptophan, polyaspartic acid, polyglutamic acid, polyasparagine, polyglutamine, polyhistidine, polylysine and polyarginine, for example. Polypeptide MS label precursors differentiated by mixtures of amino acids or derivatized amino acids generate masses having even or odd election ion with or without radicals. In some examples, polypeptides are able to be modified by catalysis. For example, by way of illustration and not limitation, phenol and aromatic amines can be added to polythreonine using a peroxidase enzyme as a catalyst. In another example, by way of illustration and not limitation, electrons can be transferred to aromatic amines using peroxidase enzyme as a catalyst. In another example, by way of illustration and not limitation, phosphates can be removed from organic phosphates using phosphatases as a catalyst.

In another example, by way of illustration and not limitation, a derivatization agent is employed as a moiety to generate an MS label from an MS label precursor. For example, dinitrophenyl and other nitrophenyl derivatives may be formed from the MS label precursor. Other examples include, by way of illustration and not limitation, esterification, acylation, silylation, protective alkylation, derivatization by ketone-base condensations such as Schiff bases, cyclization, formation of fluorescent derivatives, and inorganic anions. The derivatization reactions can occur in microreaction prior to MS analysis but after affinity reaction or be used to generate MS label precursors conjugated to affinity reagents.

In some examples, the MS label precursor can comprise an isotope such as, but not limited to, $^{2}H$, $^{13}C$, and $^{18}O$, for example, which remains in the MS label that is derived from the MS label precursor. The MS label can be detected by the primary mass or a secondary mass after ionization. In some examples, the MS label precursor is one that has a relatively high potential to cause a bond cleavage such as, but not limited to, alkylated amines, acetals, primary amines and amides, for example, where the MS label can generate a mass that has even or odd election ion with or without radicals. Selection of the polypeptide can generate a unique MS spectral signature.

As mentioned above, the alteration agent may be an enzyme (which includes pseudoenzymes). In some examples, catalysis can occur with water insoluble enzyme derivatives immobilized with, for example, silica gels, charcoals, DEAE-cellulose, DEAE-SEPHADEX (cross-linked dextran gel, commercially available from Sigma Aldrich), cellulose citrate, kaolinite, cellulose phosphate, acid clay, AMBERLITE XE-97 (carboxylic cation exchange resin manufactured by Rohm & Haas), carboxymethyl cellulose, glass, quartz, dowex-50, starch gel, polyacrylamide gel, poly amino acids, or aminobenzyl cellulose. Cross-linking agents can be used to immobilize the enzyme. Such cross-linking agents include, but are not limited to, glutaraldehyde, dimethyl adipimidate, carbodiimide, maleic anhydride, MDA methylenedianiline, hydrazide, and acyl azides, for example.

In some examples, an enzyme for purposes in accordance with the principles described herein is any enzyme with a high turnover rate that can convert as an enzyme substrate (such as an MS label precursor) into an MS label that is detected by the mass detector of a mass spectrometer in the presence of the un-converted substrate. The enzyme should not be in the sample tested or, if present in the sample, it must be removed from the sample prior to testing. Examples of enzymes suitable for this purpose include, but are not limited to, phosphatases (e.g., alkaline phosphatase, lipid phosphatases, tyrosine phosphatase, serine phosphatase, threonine phosphatase, and histidine phosphatase); oxidases (e.g., horse radish peroxidase, copper amine oxidase, D-amino acid oxidase, galactose oxidase, plasma amine oxidase, tryptophan peroxidase, uricase oxidase, and xanthine oxidase); β-galactosidase; transferases (e.g., D-alanine transferase, glycosyl transferase, acyl transferase, alkyl transferase, aryl transferase, single carbon transferase, ketone transferase, aldehyde transferase, nitrogenous transferase, phosphorus transferase, sulfur transferase, and pentosyl transferase); peptidases (e.g., pepsin, papain, rennin (chymosin), renin, thrombin, trypsin, matrix metallopeptidase, cathespin, cysteine protease, and carboxypeptidase); aldolases (e.g., carboxyl aldolase, aldehyde aldolase, oxo acids, tryptophanase); fatty acid enzymes (e.g., fatty acid amine hydrolase, fatty acid synthase, and choline acetyltransferase), for example, and combinations of two or more of the above (e.g., two or more of alkaline phosphatase, acid phosphatase, an oxidase, β-galactosidase, peroxidase, acylase, asparaginase, catalase, chymotrypsin, amylase, glucoamylase, glucose oxidase, glucose-6-phosphate dehydrogenase, hexokinase, invertase, lipase, phosphoglucomutase, ribonuclease, acetylcholinesterase, alcohol dehydrogenase, aldolase, cholinesterase, citrate synthetase, urease, amylglucosidase, carboxypeptidase, cholinesterase, luciferase, ribonuclease, pyruvate kinase, and subtilopeptidase).

Substrates for the enzymes are MS label precursors that comprise an MS label that is released by the action of the enzyme on the substrate. Such MS labels that may be part of an enzyme substrate include, by way of illustration and not limitation, phenols (from substrates such as, for example, p-nitrophenyl phosphate, p-nitrophenyl-β-D-galactoside, amino acids, peptides, carbohydrates (6-phospho-D-gluconate), fatty acids (acetyl-CoA), alkyl amines, glycerols,); and naphthols (from substrates such as, for example, p-nitronaphthyl phosphate, p-nitro-naphthyl-β-D-galactoside); for example.

Metals that may be employed to release an MS label from a moiety attached to an affinity agent include, but are not limited to, transition metals (e.g., palladium, platinum, gold, ruthenium, rhodium, or iridium), chelated metals (e.g., iron, copper, cobalt, magnesium complexed by ethylenediaminetetraacetate (EDTA), N-(2-hydroxyethyl)-ethylenediaminetriacetic acid (HEDTA), or trans-1,2-cyclohexanediaminetetraacetic acid (CDTA), for example), metal oxidants (e.g., sodium hypochlorite, potassium periodate, silver oxide, chromic acid, potassium permanganate, and sodium perborate) and metal reductants (e.g., lithium aluminum hydride, sodium borohydride, sodium ascorbate, phosphites, and sodium), for example.

The MS label can be detected directly or the released MS label can be further reacted with another compound to form a derivative MS label, which is detected by MS techniques. A derivative MS label is a compound that is formed from an MS label that is obtained from the MS label precursor where the compound also is detectable by MS techniques. This approach of forming a derivate MS label further enhances the multiplexing capability of methods in accordance with the principles described herein. For example, a released phenol or naphthol can couple to an aromatic amine in the presence of a peroxidase (see, for example, U.S. Pat. No. 5,182,213, the relevant disclosure of which is incorporated herein by reference). In one example, a released naphthol is coupled with a phenylenediamine such as, for example, α-phenylenediamine dihydrochloride, in the presence of a peroxidatively active substance in an alkaline medium to produce a derivative MS label. Multiplexing may be achieved using different naphthols and/or different phenylenediamines.

Internal standards are an important aspect of mass spectral analysis. In some examples, a second mass label can be added that can be measured (as an internal standard) in addition to the MS label used for detection of the rare target molecule. The internal standard has a similar structure to the MS label with a slight shift in mass. The internal standards can be prepared that comprise additional amino acids or derivatized amino acids. Alternatively, the internal standard can be prepared by incorporating an isotopic label such as, but not limited to $^{2}H$ (D), $^{13}C$, and $^{18}O$, for example. The MS isotope label has a mass higher than the naturally-occurring substance. For example, the isotope labeled MS labels, for example, glycerol-C-d7, sodium acetate-C-d7, sodium pyruvate-C-d7, D-glucose-C-d7, deuterated glucose, and dextrose-C-d7, would serve as internal standards for glycerol, sodium acetate, sodium pyruvate, glucose and dextrose, respectively.

An MS label precursor or an alteration agent may be attached to an affinity agent (to yield a modified affinity agent) covalently either directly by a bond or through the intermediacy of a linking group. In some embodiments, the preparation of a modified affinity agent may be carried out by employing functional groups suitable for attaching the MS label precursor or the alteration agent, to the affinity agent by a direct bond. The nature of the functional groups employed is dependent, for example, on one or more of the nature of the MS label precursor, the nature of the alteration agent, and the nature of the affinity agent including the nature of one or more different particles such as, e.g., carrier particles and label particles that may be part of the affinity agent. A large number of suitable functional groups are available for attaching to amino groups and alcohols; such functional groups include, for example, activated esters including, e.g., carboxylic esters, imidic esters, sulfonic esters and phosphate esters; activated nitrites; aldehydes; ketones; and alkylating agents.

The linking group may be a chain of from 1 to about 60 or more atoms, or from 1 to about 50 atoms, or from 1 to about 40 atoms, or from 1 to 30 atoms, or from about 1 to about 20 atoms, or from about 1 to about 10 atoms, each independently selected from the group normally consisting of carbon, oxygen, sulfur, nitrogen, and phosphorous, usually carbon and oxygen. The number of heteroatoms in the linking group may range from about 0 to about 8, from about 1 to about 6, or about 2 to about 4. The atoms of the linking group may be substituted with atoms other than hydrogen such as, for example, one or more of carbon, oxygen and nitrogen in the form of, e.g., alkyl, aryl, aralkyl, hydroxyl, alkoxy, aryloxy, or aralkoxy groups. As a general rule, the length of a particular linking group can be selected arbitrarily to provide for convenience of synthesis with the proviso that there is minimal interference caused by the linking group with the ability of the linked molecules to perform their function related to the methods disclosed herein.

The linking group may be aliphatic or aromatic. When heteroatoms are present, oxygen will normally be present as oxy or oxo, bonded to carbon, sulfur, nitrogen or phosphorous; sulfur will be normally be present as thioether or thiono; nitrogen will normally be present as nitro, nitroso or amino, normally bonded to carbon, oxygen, sulfur or phosphorous; phosphorous will be normally bonded to carbon, sulfur, oxygen or nitrogen, usually as phosphonate and phosphate mono- or diester. Functionalities present in the linking group may include esters, thioesters, amides, thioamides, ethers, ureas, thioureas, guanidines, azo groups, thioethers, carboxylate and so forth. The linking group may also be a macro-molecule such as polysaccharides, peptides, proteins, nucleotides, and dendrimers.

In some embodiments the MS label precursor, or the alteration agent, as the case may be, and the affinity agent may be linked together non-covalently. Members of a binding pair, usually a specific binding pair, are employed where one member is linked to the affinity agent and the other member is linked to the MS label precursor or to the alteration agent. Binding of the binding pair members results in the non-covalent linking of the affinity agent and the MS label precursor or the alteration agent. The binding pair members may be linked directly to one or both of the MS label precursor, or the alteration agent, and the affinity agent or indirectly through the intermediacy of a linking group, the nature of which is discussed above. In some examples, the members of the specific binding pair have a relatively high binding constant such as, by way of illustration and not limitation, avidin (streptavidin)-biotin binding, fluorescein (FITC) and antibody for FITC, rhodamine (Texas red) and antibody for rhodamine, digitonin (DIG) and antibody for DIG, non-human species antibody (e.g., goat, rabbit, mouse, chicken, sheep) and anti-species antibody, for example.

The modified affinity agents can be prepared by linking each different affinity agent in separate, individual reactions to the MS label precursor or the alteration agent and then combining the modified affinity agents to form a mixture comprising the modified affinity agents. Alternatively, the different affinity agents can be combined and the reaction to link the affinity agents to the MS label precursor or the alteration agent can be carried out on the combination. This allows the method to be multiplexed for more than one result at a time.

An amount of each different modified affinity agent that is employed in the methods of the invention is dependent for example on one or more of the nature and potential amount of each different population of target rare molecules, the nature of the MS label, the nature of the affinity agent, the nature of a cell if present, the nature of a particle if employed, and the amount and nature of a blocking agent if employed. In some examples, the amount of each different modified affinity agent employed is about 0.001 μg/μL to about 100 μg/μL, or about 0.001 μg/μL to about 80 μg/μL, or about 0.001 μg/μL to about 60 μg/μL, or about 0.001 μg/μL to about 40 μg/μL, or about 0.001 μg/μL to about 20 μg/μL, or about 0.001 μg/μL to about 10 μg/μL, or about 0.5 μg/μL to about 100 μg/μL, or about 0.5 μg/μL to about 80 μg/μL, or about 0.5 μg/μL to about 60 μg/μL, or about 0.5 μg/μL to about 40 μg/μL, or about 0.5 μg/μL to about 20 μg/μL, or about 0.5 μg/μL to about 10 μg/μL.

The number of alteration agents employed may be one per MS label precursor, or one per two MS label precursors, or one per three MS label precursors up to one per all MS label precursors employed depending on one or more of the nature of the MS label precursor, the nature of the alteration agent, whether the alteration agent is free in the medium or part of a modified affinity agent, and the nature and number of different affinity reagents used. For example, where each of the MS label precursors include a labile ester or a labile amide linkage of different MS labels to the affinity agents, a single alteration agent may be employed that results in hydrolysis of the disulfide, ester or amide linkages to yield the different MS labels. In other examples utilizing one alteration agent, or fewer alteration agents than the number of MS label precursors, may be employed. In another example, a different alteration agent can be used to generate an MS label for each different type of affinity agent used.

The combination comprising the sample (optionally concentrated) and the modified affinity agents in the aqueous medium is treated by holding for a period of time and at a temperature for binding of the modified affinity agents to target rare molecules on the cells or on the particle reagents. For each modified affinity agent that comprises an alteration agent, an MS label precursor upon which the alteration agent acts is included in the combination wherein the MS label precursor is converted to the MS label. In some examples, an additional moiety is added where the alteration agent facilitates the reaction of the moiety with the MS label precursor to yield an MS label. In some examples, the modified affinity agent comprises an MS label precursor and the alteration agent is included in the combination as an unbound substance in the medium. In this example, the alteration agent acts upon the MS label precursor of the affinity agent to produce an MS label. In some examples, a first alteration agent is employed that releases an entity that comprises an MS label precursor from the affinity agent and a second alteration agent is subsequently employed to facilitate the formation of an MS label from an MS label precursor.

The temperature and duration of this treatment is dependent for example on the nature of the sample, the nature of the target rare molecules, the nature of the non-rare molecules, the nature of the modified affinity agents, the nature of the MS label precursors, and the nature of the alteration agents. In some examples, moderate temperatures are normally employed and usually constant temperature, preferably, room temperature. Temperatures during holding a period normally range from about 5° C. to about 99° C. or from about 15° C. to about 70° C., or about 20° C. to about 45° C., for example. The holding period is about 0.2 seconds to about 24 hours, or about 1 second to about 6 hours, or about 2 seconds to about 1 hour, or about 1 to about 15 minutes, for example. The time period depends on, for example, the temperature of the medium and the rate of binding of the various reagents.

Modified affinity agents, i.e., affinity agents that have been acted upon by an alteration agent, which have become bound to target rare molecules, optionally, are separated from modified affinity agents that have not become bound to target molecules. In some examples, this separation involves reducing the number of non-rare molecules in the sample.

Contact of the treated sample with the essentially non-absorbent membrane is continued for a period of time sufficient to achieve retention of the target rare cells or the particle-bound target rare molecules on a surface of the essentially non-absorbent membrane to obtain a surface of the essentially non-absorbent membrane having different populations of target rare cells or the particle-bound target rare molecules as discussed above. The period of time may be dependent for example on one or more of the nature and size of the different populations of target rare cells or particle-bound target rare molecules, the nature of the porous matrix, the size of the pores of the porous matrix, the level of vacuum applied to the blood sample on the porous matrix, the volume to be filtered, and the surface area of the porous matrix. In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

The retentate is subjected to a second alteration agent that facilitates the formation of an MS label from the MS label precursor from the affinity agent if the first alteration agent does not facilitate the formation of an MS label from the MS label precursor.

The retentate is subjected to MS analysis to determine the presence and/or amount of each different MS label. The presence and/or amount of each different MS label are related to the present and/or amount of each different population of target rare cells and/or particle-bound target rare molecules.

MS analysis determines the mass-to-charge ratio (m/z) of molecules for accurate identification and measurement. The MS method may ionize the molecules into masses as particles by several techniques that may include, but are not limited to, atmospheric pressure chemical ionization (APCI), electrospray ionization (ESI), inductive electrospray ionization (iESI), chemical ionization (CI), and electron ionization (EI), fast atom bombardment (FAB), field desorption/field ionization (FC/FI), thermospray ionization (TSP), nanospray ionization, for example. The masses are filtered and separated in the mass detector by several techniques that include, by way of illustration and not limitation, Time-of-Flight (TOF), ion traps, quadrupole mass filters, sector mass analysis, multiple reaction monitoring (MRM), and Fourier transform ion cyclotron resonance (FTICR). The MS method detects the molecules using, for example, a microchannel plate, electron multiplier, or Faraday cup. The MS method can be repeated as a tandem MS/MS method, in which charged mass particles from a first MS are separated into a second MS.

Mass analyzers include, but are not limited to, quadrupoles, time-of-flight (TOF) analyzers, magnetic sectors, Fourier transform ion traps, and quadrupole ion traps, for example. Tandem (MS-MS) mass spectrometers are instruments that have more than one analyzer. Tandem mass spectrometers include, but are not limited to, quadrupole-quadrupole, magnetic sector-quadrupole, quadrupole-time-of-flight, for example. The detector of the mass spectrometer may be, by way of illustration and not limitation, a photomultiplier, an electron multiplier, or a micro-channel plate, for example.

Following the analysis by mass spectrometry, the presence and/or amount of each different mass spectrometry label is related to the present and/or amount of each different population of target rare cells and/or the particle-bound target rare molecules. The relationship between the MS label and a target molecule is established by the modified affinity agent employed, which is specific for the target molecule. Calibrators are employed to establish a relationship between an amount of signal from an MS label and an amount of target rare molecules in the sample. The samples may be subjected to further analysis.

As mentioned above, the essentially non-absorbent membrane may comprise more than one pore and the electrical field may be activated to selectively release droplets from an individual pore. The released droplets are subjected to mass spectrometry analysis to determine an area adjacent the individual pore where a particular MS label is located. The liquid on the membrane corresponding to the area is removed for analysis. The liquid adjacent the individual pore may be removed by any of the methods mentioned above. Methods for analysis include, but are not limited to immunoassays, enzyme amplification, cell filtration, nucleic acid sequencing, mass analysis, chemical analysis, nucleic acid amplification, nucleic acid expression, cell growth and cellular response assays, for example, or combinations of two or more thereof.

In one example, sample is collected into a container with a suitable cell buffer. The collected sample is subjected to filtration to concentrate the number of cell-bound target rare molecules over that of other molecules in the sample such as, for example, non-rare cells. An affinity agent that comprises an alteration agent linked to an antibody that is specific for the cell-bound target rare molecule is combined with the concentrated sample retained on an essentially non-absorbent membrane of a filtration device. After a suitable incubation period, the membrane is washed with a buffer. An MS label precursor is added to the sample on the membrane. The alteration agent of the affinity agent is part of an immune complex comprising the affinity agent and the cell-bound target molecule. If the target rare molecule is present in the sample, the alteration agent acts upon the MS label precursor to produce an MS label that corresponds to the target rare molecule. The essentially non-absorbent membrane is subjected to an electric field and the MS label is collected. In some embodiments, spray liquid or spray solvent is added to a well comprising the essentially non-absorbent membrane, which is exposed to the electrical field, and optionally a vacuum, to release droplets of the liquid from the porous membrane. If the target rare molecule is present in the sample, the MS label will give a distinctive spectrum that corresponds to the target rare molecule. This spectrum can be correlated to concentration and the position of the rare cell on the membrane. The position of the rare cell on the membrane can identify where to remove the rare cell for further analysis. In the example above, detection of only one target rare molecule is depicted; however, it is to be appreciated that any number of target rare molecules may be determined in a single method on a single sample using various MS label precursors as discussed above as discussed above.

In another example, sample is collected into a container with a suitable cell buffer. The collected sample is subjected to filtration to concentrate the number of cell-bound target rare molecules over that of other molecules in the sample such as, for example, non-rare cells. An affinity agent that comprises an MS label precursor linked to an antibody that is specific for the cell-bound target rare molecule is combined with the concentrated sample retained on an essentially non-absorbent membrane of a filtration device. After a suitable incubation period, the membrane is washed with a buffer. An alteration agent is added to the sample on the membrane. The MS label precursor of the affinity agent is part of an immune complex comprising the affinity agent and the cell-bound target molecule. If the target rare molecule is present in the sample, the alteration agent acts upon the MS label precursor to produce an MS label that corresponds to the target rare molecule. The essentially non-absorbent membrane is subjected to an electric field and the MS label is collected. In some embodiments, spray liquid or spray solvent is added to a well comprising the essentially non-absorbent membrane, which is exposed to the electrical field, and optionally a vacuum, to release droplets of the liquid from the porous membrane. If the target rare molecule is present in the sample, the MS label will give a distinctive spectrum that corresponds to the target rare molecule. This spectrum can be correlated to concentration and the position of the rare cell on the membrane. In the above example, detection of only one target rare molecule is depicted; however, it is to be appreciated that any number of target rare molecules may be determined in a single method on a single sample using various MS label precursors as discussed above as discussed above.

In another example, sample is collected into a container and added to the essentially non-absorbent membrane in diluted or undiluted form. In this example, the target rare molecule is non-particulate, i.e., the target rare molecule is not bound to a cell or other particle. The collected sample is combined with a particle reagent that comprises a particle to which is attached an antibody for the target rare molecule. After an incubation period to permit binding of the non-cell-bound target rare molecule to the antibody on the particle to give particle-bound non-cell-bound target rare molecule, the sample is subjected to filtration to concentrate the number of particle-bound non-cell-bound target rare molecules over that of other molecules in the sample such as, for example, non-rare cells. Sample retained on the surface of the filtration device is washed with a suitable buffer. An affinity agent that comprises an alteration agent linked to an antibody that is specific for the particle-bound non-cell-bound target rare molecule is combined with the concentrated sample retained on a membrane of a filtration device. After a suitable incubation period, the membrane is washed with a buffer. An MS label precursor is added to the sample on the membrane. The alteration agent of the affinity agent is part of an immune complex comprising the affinity agent and the particle-bound non-cell-bound target molecule. If the target rare molecule is present in the sample, the alteration agent acts upon the MS label precursor to produce an MS label that corresponds to the target rare molecule. The essentially non-absorbent membrane is subjected to an electric field and the MS label is collected. In some embodiments, spray liquid or spray solvent is added to a well comprising the essentially non-absorbent membrane, which is exposed to the electrical field, and optionally a vacuum, to release droplets of the liquid from the porous membrane. If the target rare molecule is present in the sample, the MS label will give a distinctive spectrum that corresponds to the target rare molecule. This spectrum can be correlated to concentration and the position of the rare cell on the membrane. In the above example, detection of only one non-cell-bound target rare molecule is depicted; however, it is to be appreciated that any number of target rare molecules (both cell-bound and non-cell bound) may be determined in a single method on a single sample using various MS label precursors as discussed above.

In another example, liquid sample is collected into a container and added to the essentially non-absorbent membrane in diluted or undiluted form. In this example, the target rare molecule is non-particulate, i.e., the target rare molecule is not bound to a cell or other particle. The collected sample is combined with a particle reagent that comprises a particle to which is attached an antibody for the target rare molecule. After an incubation period to permit binding of the non-cell-bound target rare molecule to the antibody on the particle to give particle-bound non-cell-bound target rare molecule, the sample is subjected to filtration to concentrate the number of particle-bound non-cell-bound target rare molecules over that of other molecules in the sample such as, for example, non-rare cells. Sample retained on the surface of the filtration device is washed with a suitable buffer. An affinity agent that comprises an MS label precursor linked to an antibody that is specific for the particle-bound non-cell-bound target rare molecule is combined with the concentrated sample retained on a membrane of a filtration device. After a suitable incubation period, the membrane is washed with a buffer. An alteration agent is added to the sample on the membrane. The MS label precursor of the affinity agent is part of an immune complex comprising the affinity agent and the particle-bound non-cell-bound target molecule. If the target rare molecule is present in the sample, the alteration agent acts upon the MS label precursor to produce an MS label that corresponds to the target rare molecule. The essentially non-absorbent membrane is subjected to an electric field and the MS label is collected. In some embodiments, spray liquid or spray solvent is added to a well comprising the essentially non-absorbent membrane, which is exposed to the electrical field, and optionally a vacuum, to release droplets of the liquid from the porous membrane. If the target rare molecule is present in the sample, the MS label will give a distinctive spectrum that corresponds to the target rare molecule. This spectrum can be correlated to concentration and the position of the rare cell on the membrane. In the example above, detection of only one non-cell-bound target rare molecule is depicted; however, it is to be appreciated that any number of target rare molecules (both cell-bound and non-cell bound) may be determined in a single method on a single sample using various MS label precursors as discussed above.

In another example, sample is collected into a container and added to the essentially non-absorbent porous membrane in dilute or undiluted form. In this example, the target rare molecule is non-particulate, i.e., the target rare molecule is not bound to a cell or other particle. The collected sample is combined with a particle reagent that comprises a particle to which is attached an antibody for the target rare molecule. After an incubation period to permit binding of the non-cell-bound target rare molecule to the antibody on the particle to give particle-bound non-cell-bound target rare molecule, the sample is subjected to filtration to concentrate the number of particle-bound non-cell-bound target rare molecules over that of other molecules in the sample such as, for example, non-rare cells. Sample retained on the surface of the filtration device is washed with a suitable buffer. An alteration agent is added to the sample on the membrane that converts the non-cell-bound target rare molecules to a MS label. After a suitable incubation period, the membrane is washed with a buffer. If the target rare molecule is present in the sample, the alteration agent acts upon the target rare molecule to produce an MS label that corresponds to the target rare molecule. The essentially non-absorbent membrane is subjected to the charge field and the MS labels collected. In some embodiments, spray liquid or spray solvent is added to a well comprising the essentially non-absorbent membrane, which is exposed to the electrical field, and optionally a vacuum, to release droplets of the liquid from the porous membrane. If the target rare molecule is present in the sample, the MS label will give a distinctive spectrum that corresponds to the target rare molecule. This spectrum can be correlated to concentration and the position of the rare cell on the membrane. In the example above, detection of only one non-cell-bound target rare molecule is depicted; however, it is to be appreciated that any number of target rare molecules (both cell-bound and non-cell bound) may be determined in a single method on a single sample using various MS label precursors as discussed above.

Examples of Methods Employing Particle Amplification

As mentioned above, in one approach, particle amplification is utilized and provides for the aggregation or clustering particles to form particle aggregates that comprise MS labels or MS label precursors.

The phrase "particle amplification" refers to the formation of aggregates or clusters of particles in which a number of label particles indicative of a single target rare molecule are enhanced. In some examples, the number of label molecules in a particle aggregate that is indicative of a target rare molecule are $10^{10}$ to 1, or $10^9$ to 1, or $10^8$ to 1, or $10^7$ to 1, or $10^6$ to 1, or $10^5$ to 1, or $10^4$ to 1, or $10^3$ to 1, or $10^2$ to 1, or 10 to 1, or $10^{10}$ to $10^2$, or $10^{10}$ to $10^3$, or $10^{10}$ to $10^4$, or $10^{10}$ to $10^5$. Particle amplification is achieved by employing a larger particle (carrier particle) associated with many smaller label particles that have many MS labels or MS label precursors associated therewith.

The term "associated with" refers to the manner in which two moieties are bound to one another. The association may be through covalent or non-covalent binding as defined above. The attachment may be accomplished by a direct bond between the two moieties or a linking group can be employed between the two moieties. Linking groups may be, for example, as described above.

The composition of the carrier particle may be, for example, as described above for capture particle entities. The size of the carrier particle is large enough to accommodate one or more label particles. The ratio of label particles to a single carrier particle may be for example $10^6$ to 1, or $10^5$ to 1, or $10^4$ to 1, or $10^3$ to 1, or $10^2$ to 1, or 10 to 1. The diameter of the carrier particle may also be dependent for example on one or more of the nature of the target rare molecule, the nature of the sample, the nature and the pore size of an essentially non-absorbent membrane, the adhesion of the particle to membrane, the surface of the particle, the surface of the membrane, the liquid ionic strength, liquid surface tension and components in the liquid, and the number, size, shape and molecular structure of associated label particles. When a porous matrix is employed in a filtration separation step, the diameter of the carrier particles should be large enough to hold a number of label particles to achieve the benefits of particle amplification but small enough to be pass through the pores of an essentially non-absorbent membrane of a filtration device. In some examples, the average diameter of the carrier particles should be at least about 0.1 microns and not more than about 1 micron, or not more than about 5 microns. In some examples, the carrier particles have an average diameter from about 0.1 microns to about 5 microns, or about 1 micron to about 3 microns, or about 4 microns to about 5 microns, about 0.2 microns to about 0.5 microns, or about 1 micron to about 3 microns, or about 4 microns to about 5 microns.

The composition of the label particle may be, for example, as described above for capture particle entities. The size of the label particles may be dependent for example on one or more of the nature and size of the carrier particle, the nature and size of the MS label, or the MS label precursor, of the alteration agent, the nature of the target rare molecule, the nature of the sample, the nature and the pore size of the essentially non-absorbent membrane, the surface of the particle, the surface of the membrane, the liquid ionic strength and, liquid surface tension and components in the liquid. In some examples, the average diameter of the label particles should be at least about 0.01 microns and not more than about 0.1 microns, or not more than about 1 micron. In some examples, the label particles have an average diameter from about 0.01 microns to about 1 micron, or about 0.01 microns to about 0.5 microns, or about 0.01 microns to about 0.4 microns, or about 0.01 microns to about 0.3 microns, or about 0.01 microns to about 0.2 microns, or about 0.01 microns to about 0.1 microns, or about 0.01 microns to about 0.05 microns, or about 0.1 microns to about 0.5 microns, or about 0.05 microns to about 0.1 microns. In some examples, the label particle may be a silica nanoparticle, which can be linked to magnetic carrier particles that have free carboxylic acid groups by ionic association.

The number of MS labels or MS label precursors associated with the label particle may be dependent for example on one or more of the nature and size of the MS label or MS label precursor, the nature and size of the label particle, the nature of the linker arm, the number and type of functional groups on the label particle, and the number and type of functional groups on the MS label precursor, for example. In some examples, the number of MS labels or MS label precursors associated with a single label particle is about $10^7$ to 1, or about $10^6$ to 1, or about $10^5$ to 1, or about $10^4$ to 1, or about $10^3$ to 1, or about $10^2$ to 1, or about 10 to 1.

As mentioned above, some examples are directed to methods of one or more different populations of target rare molecules in a sample suspected of containing the one or more different populations of rare molecules and non-rare molecules. The sample that has an enhanced concentration of the one or more different populations of target rare molecules over that of the non-rare molecules wherein the target rare molecules are in particulate form is incubated with, for each different population of target rare molecules, an affinity agent that comprises a binding partner that is specific for and binds to a target rare molecule of one of the populations of the target rare molecules. The affinity agent comprises an MS label precursor or a first alteration agent. For each different population of target rare molecules, the affinity agent comprises a particle reagent. The first alteration agent facilitates the formation of an MS label from the MS label precursor or releases an entity that comprises the MS label precursor from the affinity agent. During the incubating, for each different population of target rare molecules, particle aggregates are formed from the particle reagent of the affinity agent. A retentate and a filtrate are formed by contacting the incubated samples with an essentially non-absorbent membrane. The retentate becomes disposed on the essentially non-absorbent membrane. Spray liquid or spray solvent is added to a well comprising the essentially non-absorbent membrane, which is exposed to an electrical field, and optionally a vacuum, to release droplets of the liquid from the porous membrane.

In some examples, vacuum is applied to the sample on the essentially non-absorbent membrane to facilitate passage of the liquid droplets through the pores of the essentially non-absorbent membrane. The level of vacuum applied may be dependent for example on one or more of the nature and size of the different populations of rare cells and/or particle reagents, the nature of the essentially non-absorbent membrane, and the size of the pores of the essentially non-absorbent membrane. In some examples, the level of vacuum applied is about 1 millibar to about 100 millibar, or about 1 millibar to about 80 millibar, or about 1 millibar to about 50 millibar, or about 1 millibar to about 40 millibar, or about 1 millibar to about 30 millibar, or about 1 millibar to about 25 millibar, or about 1 millibar to about 20 millibar, or about 1 millibar to about 15 millibar, or about 1 millibar to about 10 millibar, or about 5 millibar to about 100 millibar, or about 5 millibar to about 80 millibar, or about 5 millibar to about 50 millibar, or about 5 millibar to about 30 millibar, or about 5 millibar to about 25 millibar, or about 5 millibar to about 20 millibar, or about 5 millibar to about 15 millibar, or about 5 millibar to about 10 millibar. The application of vacuum is coordinated with application of the electrical field so the liquid droplets can be selectively released from individual microwells comprising an essentially non-absorbent membrane in accordance with the principles described herein.

The droplets are subjected to MS analysis to determine the presence and/or amount of each different MS label. The presence and/or amount of each different MS label is related to the present and/or amount of each different population of non-cellular target rare molecules in the sample. In this manner samples may be identified for further analysis. In one approach, the essentially non-absorbent membrane containing material of interest may be removed by any convenient method. Examples of such methods include, but are not limited to, punching out the portion of the essentially non-absorbent membrane of interest or by filtration, for example.

The size of the particle aggregates is dependent on one or more of the nature and size of the capture particle, the nature and size of the carrier particle, the nature and size of the label particle, the nature and size of the linking groups, the nature and size of the MS label or the MS label precursor, the nature of the alteration agent, the nature of the target rare molecule, the nature of the sample, the nature and the pore size of a filtration matrix, the surface of the particle, the surface of the matrix, the liquid ionic strength and, liquid surface tension and components in the liquid, for example. In some examples in accordance with the principles described herein, the average diameter of the particle aggregates is at least about 0.1 microns and not more than about 500 microns, or not more than about 1,000 microns. In some examples, the particle aggregates have an average diameter from about 0.1 microns to about 1,000 microns, or about 0.1 microns to about 500 microns, or about 0.1 microns to about 100 microns, or about 0.1 microns to about 10 microns, or about 0.1 microns to about 5 microns, or about 0.1 microns to about 1 micron, or about 1 micron to about 10 microns, or about 10 microns to about 500 microns, or about 10 microns to about 100 microns, for example.

In one example, the target rare molecule is attached to the surface of a cell on the order of about 10 microns (m). Carrier particles having an average diameter of about 1 μm in this example are linked by means of a first linking group to a specific binding partner such as, for example, an antibody for the target rare molecule. A second linking group links additional carrier particles to one another in a linear manner. In this example, the number of carrier particles per cell is about 1,000. Furthermore, there are approximately 100 label particles (about 200 nm in diameter) per each carrier particle linked thereto by means of a third linking group. For each label particle there are about $10^5$ MS labels (Mass labels) linked thereto by means of a fourth linking group. In this example, the MS labels have a size of about 1 nm. The linking groups may be chosen from any linking group as described above and two or more thereof may be the same or each of the linking groups may be different from one another. In some examples, one or more of the linking groups have a cleavable moiety so that, for example, carrier particles may be cleaved from one another or from the cell and/or label particles may be cleaved from the carrier particles, and/or MS labels or MS label precursors may be cleaved from the label particles. Cleavage of the various linking groups may be carried out sequentially where the cleavable moieties of the linking groups differ from one another.

As mentioned above, one or more linking groups may comprise a cleavable moiety that is cleavable by a cleavage agent. The nature of the cleavage agent is dependent on the nature of the cleavable moiety. Cleavage of the cleavable moiety may be achieved by chemical or physical methods, involving one or more of oxidation, reduction, solvolysis, e.g., hydrolysis, photolysis, thermolysis, electrolysis, sonication, and chemical substitution, for example. Examples of cleavable moieties and corresponding cleavage agents, by way of illustration and not limitation, include disulfide that may be cleaved using a reducing agent, e.g., a thiol; diols that may be cleaved using an oxidation agent, e.g., periodate; diketones that may be cleaved by permanganate or osmium tetroxide; diazo linkages or oxime linkages that may be cleaved with hydrosulfite; β-sulfones, which may be cleaved under basic conditions; tetralkylammonium, trialkylsulfonium, tetralkylphosphonium, where the α-carbon is activated, e.g., with carbonyl or nitro, that may be cleaved with base; ester and thioester linkages that may be cleaved using a hydrolysis agent such as, e.g., hydroxylamine, ammonia or trialkylamine (e.g., trimethylamine or triethylamine) under alkaline conditions; quinones where elimination occurs with reduction; substituted benzyl ethers that can be cleaved photolytically; carbonates that can be cleaved thermally; metal chelates where the ligands can be displaced with a higher affinity ligand; thioethers that may be cleaved with singlet oxygen; hydrazone linkages that are cleavable under acidic conditions; quaternary ammonium salts (cleavable by, e.g., aqueous sodium hydroxide); trifluoroacetic acid-cleavable moieties such as, e.g., benzyl alcohol derivatives, teicoplanin aglycone, acetals and thioacetals; thioethers that may be cleaved using, e.g., HF or cresol; sulfonyls (cleavable by, e.g., trifluoromethane sulfonic acid, trifluoroacetic acid, or thioanisole); nucleophile-cleavable sites such as phthalamide (cleavable, e.g., with substituted hydrazines); ionic association (attraction of oppositely charged moieties) where cleavage may be realized by changing the ionic strength of the medium, adding a disruptive ionic substance, lowering or raising the pH, adding a surfactant, sonication, and adding charged chemicals; and photocleavable bonds that are cleavable with light having an appropriate wavelength such as, e.g., UV light at 300 nm or greater.

In one example, a cleavable linkage may be formed using conjugation with N-succinimidyl 3-(2-pyridyldithio)propionate) (SPDP), which comprises a disulfide bond. For example, a label particle comprising an amine functionality is conjugated to SPDP and the resulting conjugate can then be reacted with a MS label comprising a thiol functionality, which results in the linkage of the MS label moiety to the conjugate. A disulfide reducing agent (such as, for example, dithiothreitol (DTT) or tris(2-carboxyethyl)phosphine (TCEP)) may be employed as an alteration agent to release a thiolated peptide as an MS label.

An example, by way of illustration and not limitation, of the formation of a particle aggregate (particle cluster) on a membrane of a filtration device is discussed next. A cell or a capture particle that has captured a non-particulate target rare molecule in a sample is contacted with a membrane of a filtration slide, wherein the size of the pores of the membrane are as described above for retaining cells or particle-bound target rare molecules. After suitable washing to remove non-particulate material and to reduce the number of non-rare molecules and non-rare cells as discussed above, a set of carrier particles as described above is added for each different population of target rare molecules where each set of the carrier particles comprise a specific binding partner specific for a different target rare molecule to be determined. The specific binding partner is linked to the carrier particle by means of a first linking group. Carrier particles are linked to one another employing a second linking group. After another washing step, label particles are added where each set of the label particles comprise an MS label or an MS label precursor for a different target rare molecule to be determined. The label particles comprise a functionality that is reactive with a functionality on the carrier particles. The reaction of the functionalities provides for the formation of a third linking group. The MS labels or the MS label precursors are bound to the label particles by means of a fourth linking group. As a result, a particle cluster is formed comprising the target rare molecule, the carrier particles, the label particles and the MS labels or MS label precursors.

In some examples, one or more of the linking groups are formed covalently as described above employing appropriate corresponding functionalities of functional groups as discussed above. In some examples, one of more of the linking groups is formed non-covalently as discussed above. Members of a binding pair, usually a specific binding pair, are employed where one member is linked to one linking group moiety and the other member is linked to a second linking group moiety. When the binding pair members bind, the linking group is formed that includes the binding pair members and the two linking group moieties. Binding of the binding pair members results in the non-covalent linking of the two linking group moieties that ultimately form the linking group. The linking group moieties may be a bond or a linking group as discussed above. As mentioned above, the members of the binding pair have a relatively high binding constant such as, by way of illustration and not limitation, avidin (streptavidin)-biotin binding, fluorescein (FITC) and antibody for FITC, rhodamine (Texas red) and antibody for rhodamine, digitonin (DIG) and antibody for DIG, non-human species antibody (e.g., goat, rabbit, mouse, chicken, sheep) and anti-species antibody, for example.

In some examples, by way of illustration and not limitation, the first linking group may involve a non-cleavable bond employing a secondary antibody linked to biotin where the secondary antibody binds to the antibody for the target rare molecule and the biotin binds to streptavidin molecules on the surface of a carrier particle. Alternatively, the antibody can be directly conjugated to the carrier particle through amide bounds to the carboxylic acids on the particle and amines on the antibody using commonly known bioconjugation methods. In another example, the first linking group may involve a cleavable linkage employing a small molecule peptide linked to biotin and attached to the antibody by a disulfide linker made by reaction with, for example, SPDP. In some examples, the second linking group may include a non-cleavable linkage where the carrier particle has streptavidin molecules on its surface and a conjugate of biotin and a small molecule such as, for example, biotin-FITC, is employed to form the linking group. When a cleavable linkage is desired for the second linking group, the biotin-FITC agent includes a cleavable moiety such as, for example, a disulfide bond. The small molecule portion, e.g., FITC portion, of the second linking group binds to a binding partner for the small molecule (e.g., an antibody for FITC) on the surface of the carrier particle. The third linking group may include a non-cleavable linkage where the linking moiety has a peptide attached to FITC or biotin by an amide bond or the third linking group may include a cleavable linkage where the linking moiety has a peptide attached to FITC or biotin by a disulfide bond. The third linking group may include an ionic linkage where the ionized amines or other groups on the label particle are attracted to the ionized carboxylic acid or other groups on the label particle. As explained above, an MS label or MS label precursor is attached to a label particle by a cleavable bond such as, but not limited to, a peptide or other MS label attached by a disulfide bond.

The phrase "small molecule" refers to a molecule having a molecular weight in the range of about 100 to about 2,000, or about 200 to about 2,000, or about 300 to about 2,000, or about 500 to about 2,000, or about 1,000 to about 2,000, or about 500 to about 1,500, or about 1,000 to about 1,500, or about 1,000 to about 1,200, for example. Examples of small molecules, by way of illustration and not limitation, include biotin, digoxin, digoxigenin, 2,4-dinitrophenyl, fluorescein, rhodamine, small peptides (meeting the aforementioned molecular weight limits), vitamin B12 and folate, for example. Examples of small molecule-binding partner for the small molecule pairs, by way of illustration and not limitation, include biotin-binding partner for biotin (e.g., avidin, streptavidin and antibody for biotin), digoxin-binding partner for digoxin (e.g., antibody for digoxin), digoxigenin-binding partner for digoxigenin (e.g., antibody for digoxigenin), 2,4-dinitrophenyl and binding partner for 2,4-dinitrophenyl (e.g., antibody for 2,4-dinitrophenyl), fluorescein-binding partner for fluorescein (e.g., antibody for fluorescein), rhodamine-binding partner for rhodamine (e.g., antibody for rhodamine), peptide-binding partner for the peptide (e.g., antibody for the peptide), analyte-specific binding partners (e.g., intrinsic factor for B12, folate binding factor for folate), for example.

Examples of small molecule peptides, which may function also as MS labels, include, by way of illustration and not limitation, peptides that comprise two or more of histidine, lysine, phenylalanine, leucine, alanine, methionine, asparagine, glutamine, aspartic acid, glutamic acid, tryptophan, proline, valine, tyrosine, glycine, threonine, serine, arginine, cysteine and isoleucine and derivatives thereof. In some examples, the peptides have a molecular weight of about 100 to about 3,000 mass units and may contain 3 to 30 amino acids. In some examples, the peptides comprise nine amino acids selected from the group consisting of tyrosine, glycine, methionine, threonine, serine, arginine, phenylalanine, cysteine and isoleucine and have masses of 1,021.2; 1,031.2; 1,033.2; 1,077.3; 1,087.3; 1,127.3; 1,137 mass units; or 3 amino acids from the above group and having masses of 335.4, 433.3, 390.5, 426.5, and 405.5 mass units. The number of amino acids in the peptide is determined by, for example, the nature of the MS technique employed. For example, when using MALDI for detection, the peptide can have a mass in the range of about 600 to about 3,000 and is constructed of about 6 to about 30 amino acids. Alternatively, when using EIS for detection, the peptide has a mass in the range of about 100 to about 1,000 and is constructed of 1 to 9 amino acids or derivatives of, for example. In some examples, the number of amino acids in the peptide label may be 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, for example.

The use of peptides as MS labels has several advantages, which include, but are not limited to, the following: 1) relative ease of conjugation to proteins, antibodies, particles and other biochemical entities; 2) relative ease with which the mass can be altered to allow many different masses thus providing for multiplexed assay formats and standards; and 3) adjustability of the mass to a mass spectrometer used. For conjugation, the peptides can have a terminal cysteine that is employed in the conjugation. For ionization, the peptides can have charged amine groups. In some examples, the amino acid peptides have N-terminal free amine and C-terminal free acid. In some examples, the amino acid peptides are isotope labeled or derivatized with an isotope. The peptides may be conjugated to a small molecule such as, for example, biotin or fluorescein, for binding to a corresponding binding partner for the small molecule, which in this example is streptavidin or antibody for fluorescein. Biotin or fluorescein may be conjugated at the N-terminal with the C-terminal being free acid.

The methods described herein involve trace analysis, i.e., minute amounts of material on the order of 1 to about 100,000 copies of rare cells or target rare molecules. Since this process involves trace analysis at the detection limits of the mass spectrometers, these minute amounts of material can only be detected when detection volumes are extremely low, for example, $10^{-15}$ liter, so that the concentrations are within the detection. Examples of methods and apparatus in accordance with the principles described herein reduce or avoid evaporation.

Obtaining reproducibility in amounts of MS label or MS label precursor released for a rare cell or a target rare molecule requires measuring the formation and essentially complete recovery of the carrier and label particles. Therefore, in one approach the carrier particles, label particles, linking group and/or MS label or MS label precursor may be made fluorescent by virtue of the presence of a fluorescent molecule such as, but not limited to, FITC, rhodamine compounds, phycoerythrin, phycocyanin, allophycocyanin, o-phthaldehyde, fluorescent rare earth chelates, amino-coumarins, umbelliferones, oxazines, Texas red, acridones, perylenes, indacines such as, e.g., 4,4-difluoro-4-bora-3a, 4a-diaza-s-indacene and variants thereof, 9,10-bis-phenylethynylanthracene, squaraine dyes and fluorescamine, for example. A fluorescent microscope may then be used to determine the location of the carrier particles, label particles, linking group, and/or MS label or MS label precursor before and after treatment. This serves as a confirmative measure of the system function and is valued for additional information on the location of the rare cell or target rare molecule on the cellular structure or a capture particle.

Kits for Conducting Methods

The apparatuses and reagents of the invention may be present in a kit useful for conveniently performing the methods of the invention. In one embodiment, a kit comprises a packaged combination of an essentially non-absorbent membrane and modified affinity agents, one for each different target rare molecule. The kit may also comprise one or more unlabeled antibodies or nucleic acid probes directed at non-rare cells so that they can be eliminated from analysis. Depending on whether the modified affinity agent comprises an MS label precursor or an alteration agent, the kit may also comprise the other of the MS label precursor or the alteration agent that is not part of the modified affinity agent. The kit may also include a substrate for a moiety that reacts with an MS label precursor to generate an MS label. In addition, the kit may also comprise one or more of a fixation agent, a permeabilization agent, and a blocking agent to prevent non-specific binding to the cells, for example. Other reagents for performing the method may also be included in the kit, the nature of such reagents depending upon the particular format to be employed. The reagents may each be in separate containers or various reagents can be combined in one or more containers depending on the cross-reactivity and stability of the reagents. The kit can further include other separately packaged reagents for conducting the method such as ancillary reagents, binders, containers for collection of samples, and supports for cells such as, for example, microscope slides, for conducting an analysis, for example.

The relative amounts of the various reagents in the kits can be varied widely to provide for concentrations of the reagents that substantially optimize the reactions that need to occur during the present methods and further to optimize substantially the sensitivity of the methods. Under appropriate circumstances one or more of the reagents in the kit can be provided as a dry powder, usually lyophilized, including excipients, which on dissolution will provide for a reagent solution having the appropriate concentrations for performing a method in accordance with the principles described herein. The kit can further include a written description of a method utilizing reagents in accordance with the principles described herein.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following examples further describe the specific embodiments of the invention by way of illustration and not limitation and are intended to describe and not to limit the scope of the invention. Parts and percentages disclosed herein are by volume unless otherwise indicated.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Release of Liquid Droplets from Membrane

A total of three essentially non-absorbent membranes were employed for testing. The first membrane was an essentially non-absorbent membrane that contained an 8×8 $mm^2$ silicon region consisting of 6400 microwells approximately 70 μm in diameter and 360 μm tall. The bottom of each well was covered by a 1 μm thick silicon nitride ($Si_3N_4$) rigid membrane with a 5 μm hole approximately centered within the well opening. The angle formed at the intersection of a surface of the membrane and the hole was 90°. The second membrane was an essentially non-absorbent 1 μm thick silicon nitride ($Si_3N_4$) rigid membrane of 8×8 $mm^2$ that consisted of a single microwell with a region containing about 108,000 pores of 5 μm diameter with the second membrane approximately centered within the microwell opening. The angle formed at the intersection of a surface of the membrane and all pore holes was 90° and did not vary by more than 1°. The third membrane was an essentially non-absorbent membrane of polycarbonate that was flexible. The third membrane was 3.7 $cm^2$ and was positioned at the bottom of a single microwell. The third membrane had about 100,000 pores of 8 μm diameter. The angle formed at the intersection of a surface of the membrane and the hole of the pore varied from 30 to 150° between individual pores.

ESI occurs when the electric field strength at a solvent-air interface is ample in magnitude to overcome the forces due to surface tension of the liquid. At this point, the liquid is drawn into a cone from which charged droplets were expelled. These droplets underwent evaporation and fission cycles to ultimately produce gas-phase ions that were drawn into the vacuum system of a mass spectrometer for analysis. In the generation of an electrospray directly from the membrane surface in this example, the solution to be sprayed must sufficiently wet the top-side of the chip (etched silicon wafer housing) which contains the microwells. A solvent which displays ideal wettability with the surface will inherently fill the wells upon solvent addition, thus providing a capillary flow for continuous solvent delivery during spray events. The back side of the $Si_3N_4$ membrane should ideally have a non-wetting interaction with the spray solvent. This type of interaction isolates the liquid to single drops on each of the 5-μm pores. The presence of individual droplets creates a high degree of curvature (compared to a flat, wetted surface) which produces greater electric field strength under the application of an electric potential, thus aiding in the formation of an electrospray. Additionally, by positioning the capillary inlet of a mass spectrometer in close proximity to the bottom side of the membrane, electric field strength is further enhanced and allows the generation of the electrospray from selected regions of the membrane, thus recovering spatial information. The spray solvent should be sufficiently polar and have a surface tension low enough to permit electrospray at electric field strengths lower than those which produce electrical breakdown of air.

Acetonitrile and methanol were selected as the spray solvents for initial tests of direct membrane spray. Experiments were performed in which the standard straight capillary for the atmospheric pressure inlet (API) of a THERMO LTQ (linear ion trap) mass spectrometer (from Thermo Electron North America LLC) was replaced with an extended capillary which was bent at a 90° angle, such that the opening was pointing up. In all experiments, the membrane was positioned with the bottom side parallel to the ground approximately 1 mm distant from the bent capillary inlet. The bottom side of the membrane and the bent capillary were illuminated using a diode laser and video was recorded with a CMOS camera.

In the first set of experiments, 50 μL of methanol (or acetonitrile) was pipetted directly onto the top side of the membrane and potential was applied by directing the plasma from an antistatic gun towards the solvent. When potential was applied in this manner, discrete spray events were visualized and recorded mass spectra showed peaks typical of spraying the same solution via nanoESI. Upon the depletion of solvent, spectra were drastically different and were characteristic of those seen when firing the antistatic gun unobstructed at the MS inlet.

Further experiments showed that a porous membrane will spray but the amount of material sprayed is variable (20% cv) and the time at which the ejection of analyte ions and charged droplets containing analyte occurs is variable as well by more than 100 msec making the trapping of ions difficult as it occurs over short time scales and with small spray volumes; thus, resulting in a method that is not quantitative. As a control, an impermeable layer having pores of fixed orientation and being flexible (causing angle of greater than 1 degree) was tested. The result with this layer was that material sprayed varied by more than 20% CV. The membrane employed having characteristics in accordance with the principles described herein yielded spray amounts that were less than 1% CV.

Figure 10:
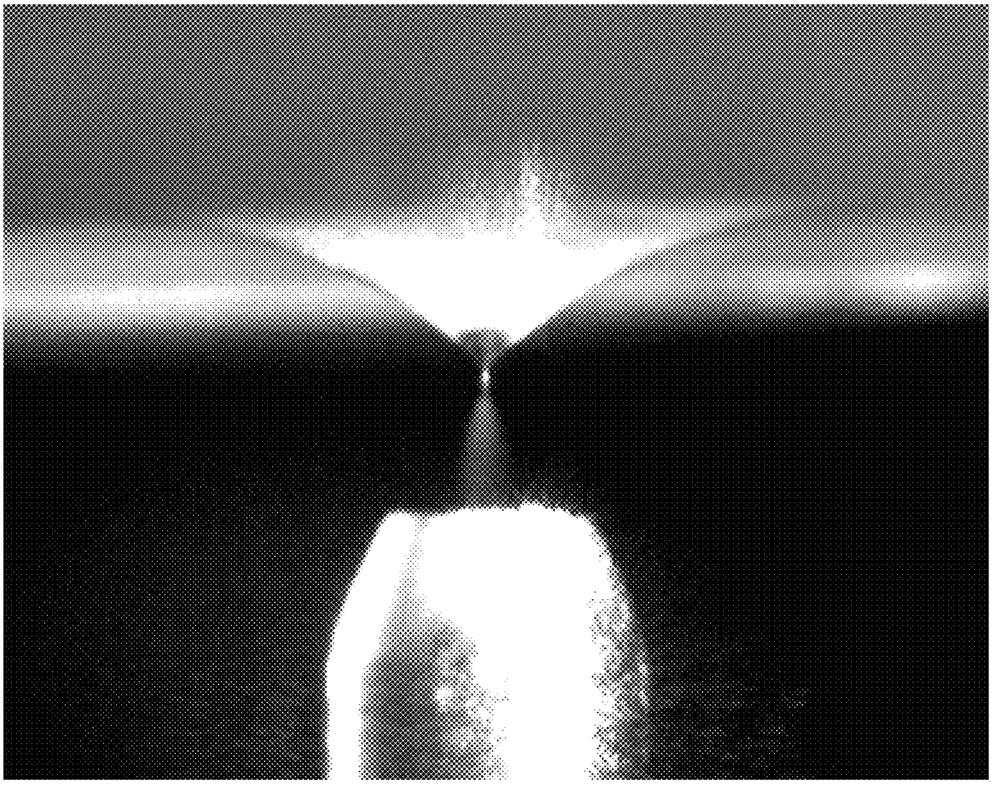
FIG. 10 is a photograph of a spray plume from an apparatus of the invention that is directed into an MS inlet.

A comparison of the performance of flexible and non-flexible membranes was made by spraying a solution containing a quaternary peptide (FC-2) from both the flexible and non-flexible membranes. This comparison was made using membranes that had previously been used to filter blood. In the case of the flexible membrane, the membrane was positioned approximately 0.5 mm above the bent MS inlet and a 6.5 kV potential was applied to a wire (the electric field generator) positioned approximately 5 mm above the membrane. A solution (25 μL of 4:1 methanol: water with 0.1% formic acid) containing the FC-2 peptide was then applied to the top of the membrane while recording MS/MS spectra of the ion m/z 412. When electrosprayed in positive mode, the FC-2 peptide produces a molecular ion at m/z 412 that when subjected to CID fragments primarily to m/z 353. In the case of the non-flexible membrane, the procedure was identical with the following changes: the voltage of the electric field generator was set to 6.0 kV and the amount of liquid applied was 5 μL. The concentration of the FC-2 peptide in each case was adjusted to 1, 10, and 100 nM. CID spectra of m/z 412 are shown in FIGS. 8A-C and FIGS. 9A-C for the flexible and non-flexible membranes, respectively. Spray formation from the flexible membrane occurred over a period of 1-3 seconds after applying liquid to the membrane and a photograph of the developed spray is shown in FIG. 10. In the case of the non-flexible membrane, a comparable spray plume was not observed, suggesting that the spray formation occurs from individual wells.

What is claimed is:

1. An apparatus comprising:

an essentially non-absorbent membrane comprising at least one pore;

a microwell comprising a back wall, side walls, and a front that is operably associated with the essentially non-absorbent membrane, wherein the back wall, the side walls, and the front define a volume within the microwell; and an electric field generator physically separate and spaced apart from the back wall and side walls of the microwell and positioned within a space behind the back wall of the microwell and aligned within the space to not be outside of the side walls of the microwell such that the electric field generator inductively imparts an electric field to a sample within the volume within the microwell defined by the back wall, the side walls, and, and the front of the microwell to operably interact with the sample in the volume within the microwell and expel a droplet of the sample through the at least one pore in the essentially non-absorbent membrane.

2. The apparatus according to claim 1, wherein the at least one pore comprises a proximal opening, a distal opening, and walls.

3. The apparatus according to claim 2, wherein the walls of the at least one pore are oriented to be 90 degrees with respect to the proximal and distal openings.

4. The apparatus according to claim 2, wherein the walls of the at least one pore taper from the proximal opening toward the distal opening.

5. The apparatus according to claim 2, wherein the walls of the at least one pore taper from the distal opening toward the proximal opening.

6. The apparatus according to claim 1, wherein the essentially non-absorbent membrane comprises a plurality of pores.

7. The apparatus according to claim 6, wherein the plurality of pores comprise the same dimensions.

8. The apparatus according to claim 6, wherein the plurality of pores comprise different dimensions.

9. The apparatus according to claim 1, wherein the apparatus further comprises a mass spectrometer.

* * * * *